(12) United States Patent
Fortune et al.

(10) Patent No.: US 11,478,621 B2
(45) Date of Patent: Oct. 25, 2022

(54) FLUID REMOVAL DEVICE

(71) Applicant: **Sim*Vivo, LLC**, Naples, FL (US)

(72) Inventors: John B. Fortune, Naples, FL (US); Jacob W. Kittell, Burlington, VT (US); Carl B. Silver, Burlington, VT (US)

(73) Assignee: **Sim*Vivo, LLC**, Naples, FL (US)

( * ) Notice: Subject to any disclaimer, the term of this patent is extended or adjusted under 35 U.S.C. 154(b) by 0 days.

(21) Appl. No.: 17/700,791

(22) Filed: Mar. 22, 2022

(65) Prior Publication Data

US 2022/0226622 A1    Jul. 21, 2022

Related U.S. Application Data

(63) Continuation of application No. 16/485,258, filed as application No. PCT/US2018/018719 on Feb. 20, 2018.

(60) Provisional application No. 62/460,124, filed on Feb. 17, 2017.

(51) Int. Cl.
  *A61M 27/00* (2006.01)
  *A61M 5/158* (2006.01)
  *A61M 1/00* (2006.01)

(52) U.S. Cl.
  CPC .............. *A61M 27/00* (2013.01); *A61M 1/86* (2021.05); *A61M 5/1582* (2013.01); *A61M 2205/32* (2013.01); *A61M 2205/502* (2013.01); *A61M 2205/583* (2013.01); *A61M 2205/8206* (2013.01); *A61M 2210/101* (2013.01)

(58) Field of Classification Search
  CPC ................ A61M 25/00; A61M 25/007; A61M 25/0021; A61M 25/0023; A61M 27/00; A61M 1/86; A61M 2210/101; A61M 25/0147
  See application file for complete search history.

(56) References Cited

U.S. PATENT DOCUMENTS 4,976,688 A * 12/1990 Rosenblum ....... A61M 25/0147
                                                    604/524
5,217,465 A    6/1993 Steppe
(Continued)

OTHER PUBLICATIONS

Edward, Vinod, Extended European Search Report regarding EU App. No. 18754888.8, dated Dec. 4, 2020.
(Continued)

*Primary Examiner* — Tatyana Zalukaeva
*Assistant Examiner* — Nhu Q. Tran
(74) *Attorney, Agent, or Firm* — STGIP, LLC; Shawn Gordon

(57) ABSTRACT

A fluid removal device is provided for removing fluid from pleural space that includes a flexible, open tube with a slight resting curve. A first channel along a greater curvature of the tube contains a plurality of cannulas that can be extended into the pleural space to infuse medications. A second channel along a lesser curvature of the tube contains a line attached to the outer portion of the tube and tension placed on the line will increase the curve of the tube to assist in the placement of the tip of the tube in a desired location in the pleural space. The tube may be connected to a portable suction/fusion device via a click connect device. The tube may also include an improved tip and a tab for extending the cannulas maintains the corridor of stability.

2 Claims, 19 Drawing Sheets

(56) References Cited

U.S. PATENT DOCUMENTS

| | | | | | |
|---|---|---|---|---|---|
| 6,042,562 | A | * | 3/2000 | Amor | A61M 25/00 |
| | | | | | 116/284 |
| 6,126,649 | A | * | 10/2000 | VanTassel | A61M 25/0147 |
| | | | | | 604/95.04 |
| 2005/0043682 | A1 | | 2/2005 | Kucklick | |
| 2008/0228174 | A1 | * | 9/2008 | Ibrahim | A61M 25/02 |
| | | | | | 604/541 |
| 2009/0143633 | A1 | * | 6/2009 | Edmundson | A61M 25/04 |
| | | | | | 604/524 |
| 2010/0130823 | A1 | * | 5/2010 | Ando | A61B 1/00078 |
| | | | | | 600/141 |
| 2011/0152842 | A1 | * | 6/2011 | Graffam | A61M 25/0052 |
| | | | | | 604/540 |
| 2012/0259206 | A1 | * | 10/2012 | Roberts | A61M 25/0105 |
| | | | | | 604/528 |
| 2015/0374959 | A1 | * | 12/2015 | Lazarus | A61M 25/0136 |
| | | | | | 604/543 |
| 2016/0074188 | A1 | * | 3/2016 | Ryan | A61F 2/962 |
| | | | | | 623/1.12 |
| 2016/0114084 | A1 | * | 4/2016 | Minskoff | A61M 1/743 |
| | | | | | 604/119 |
| 2017/0348475 | A1 | * | 12/2017 | Hiemenz | A61M 3/0287 |

OTHER PUBLICATIONS

EPO, Communication under Rule 71(3) EPC regarding EU App. No. 18754888.8, dated Sep. 13, 2021.

\* cited by examiner

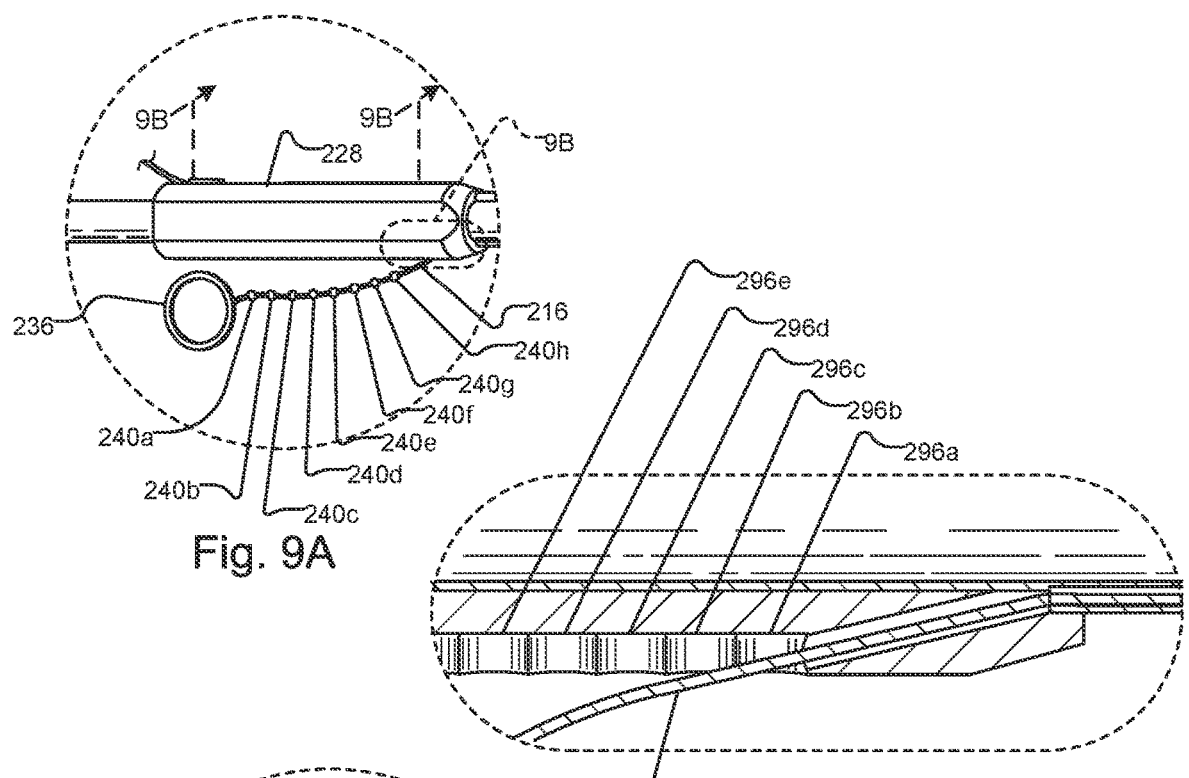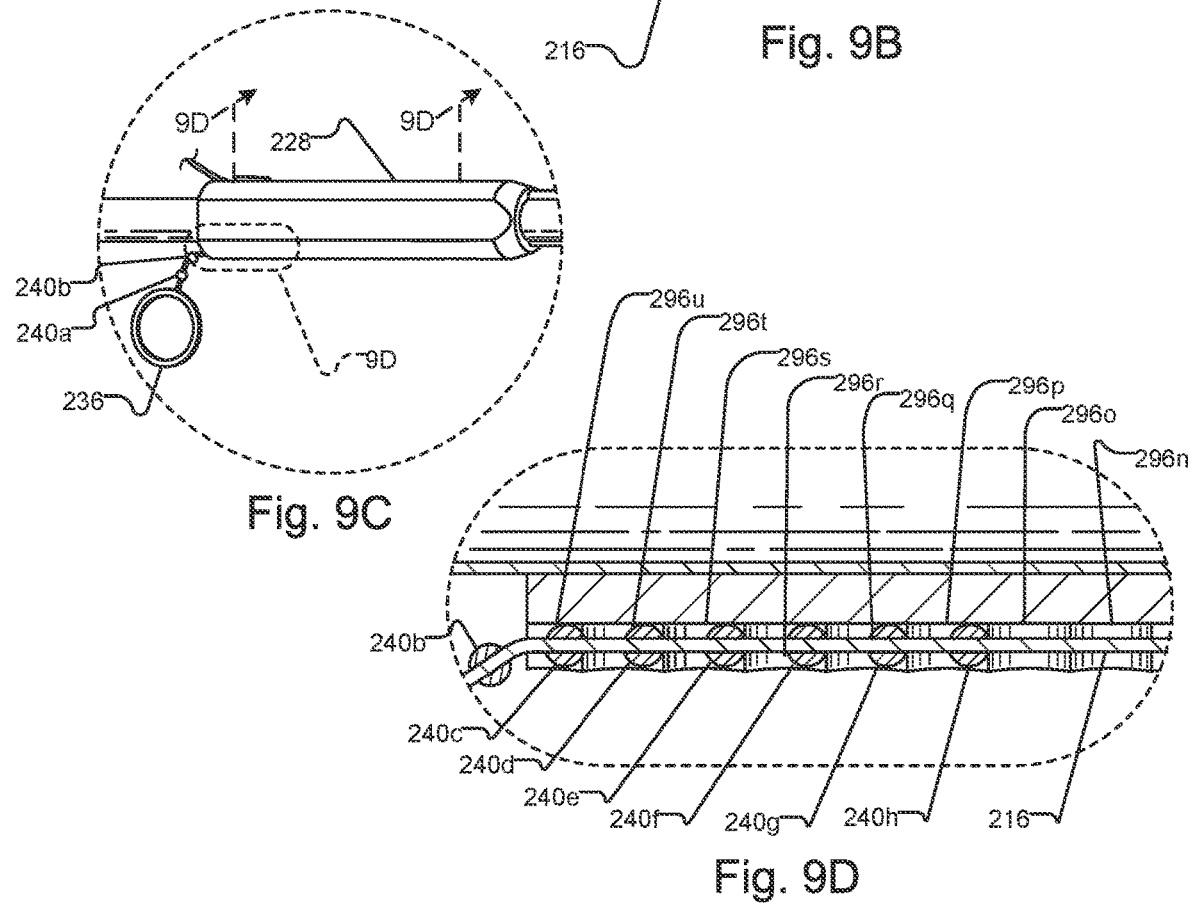

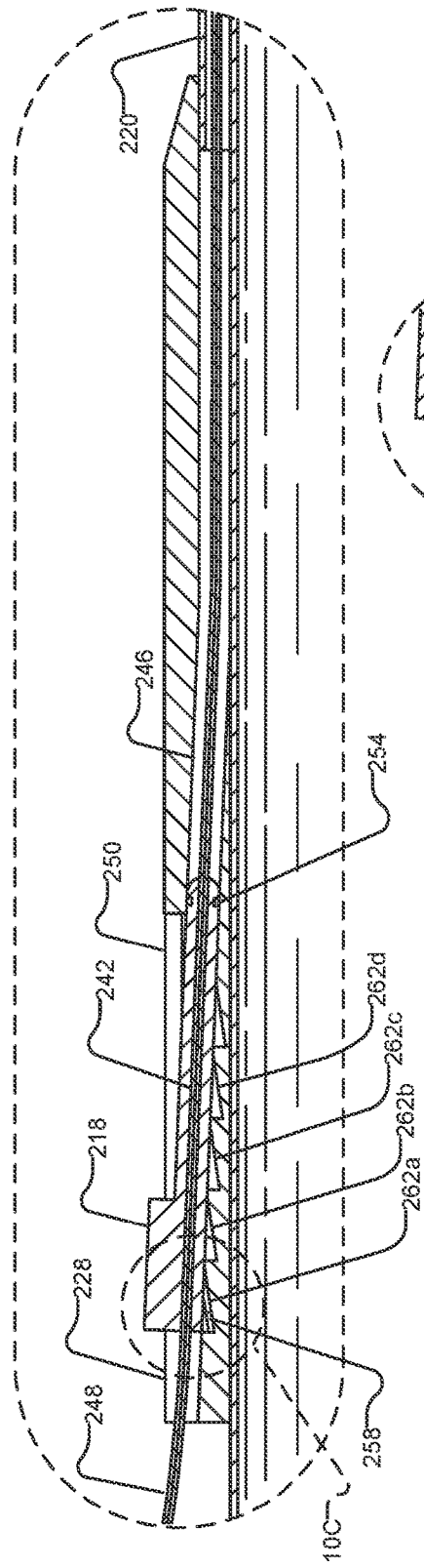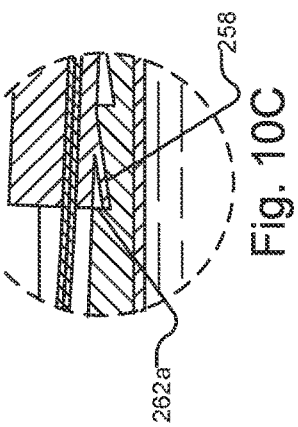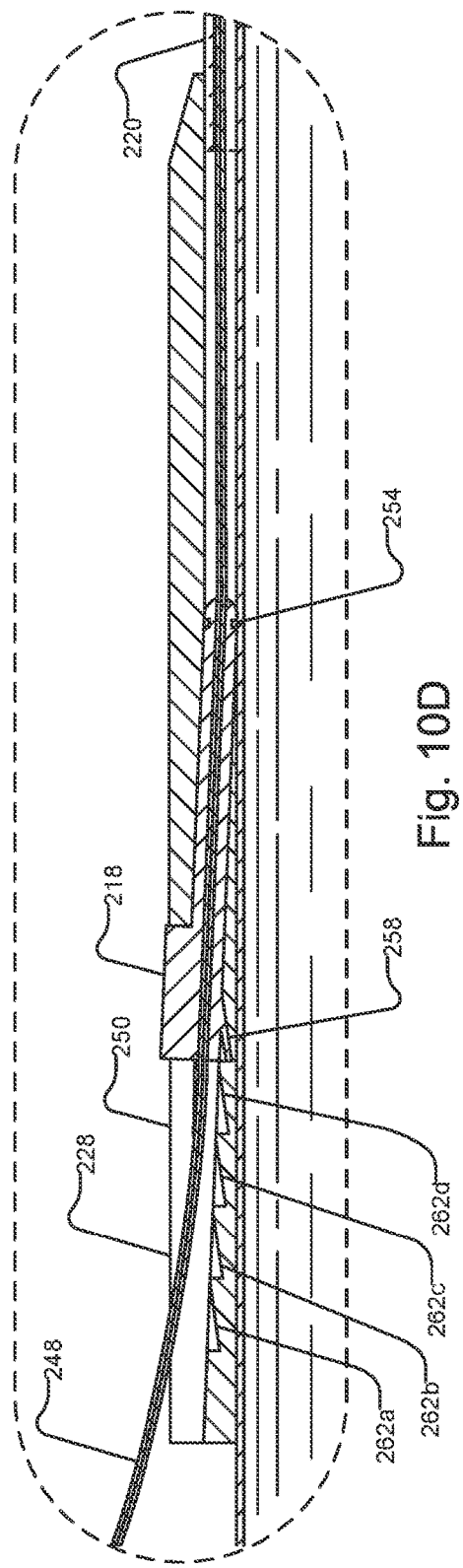

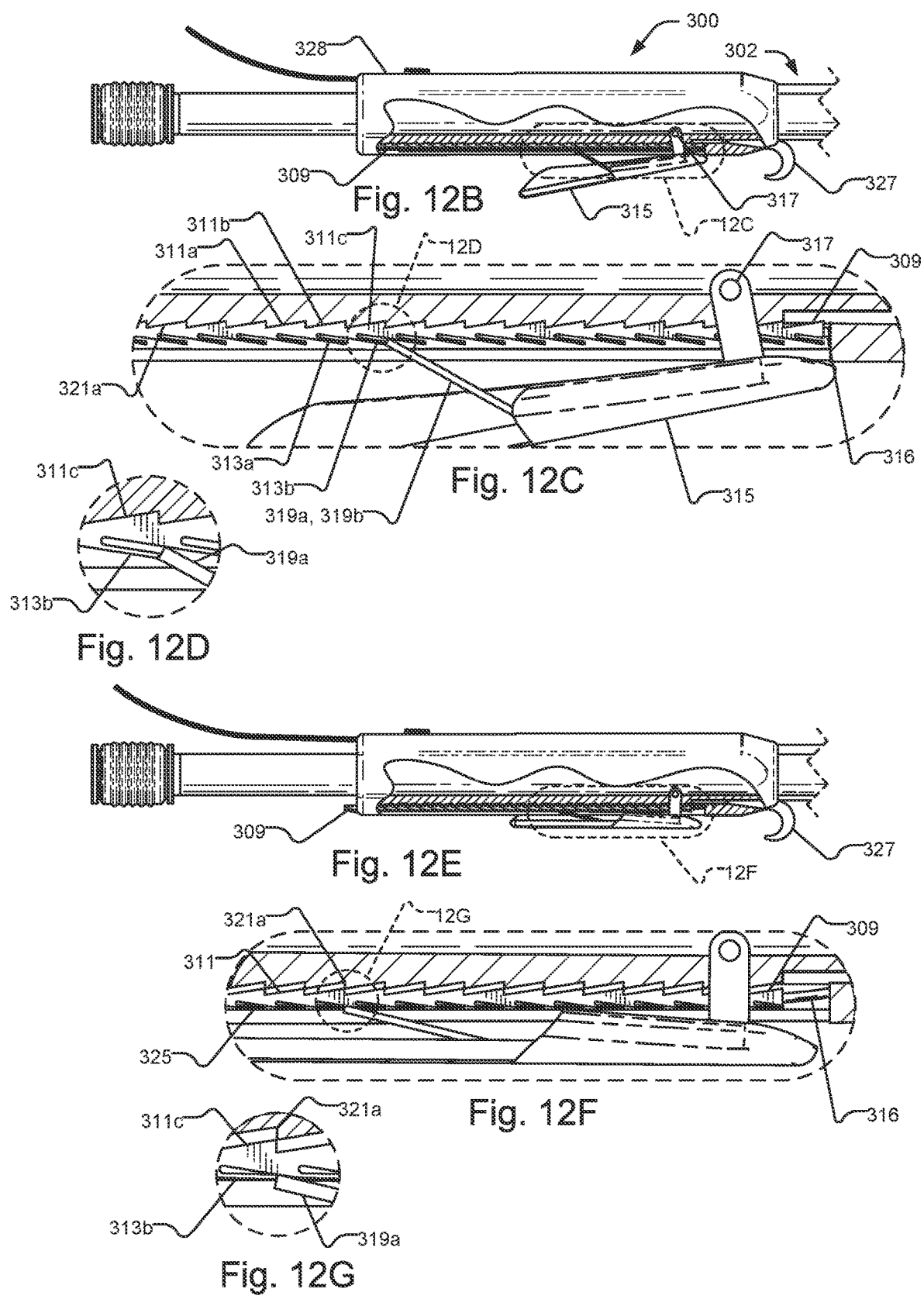

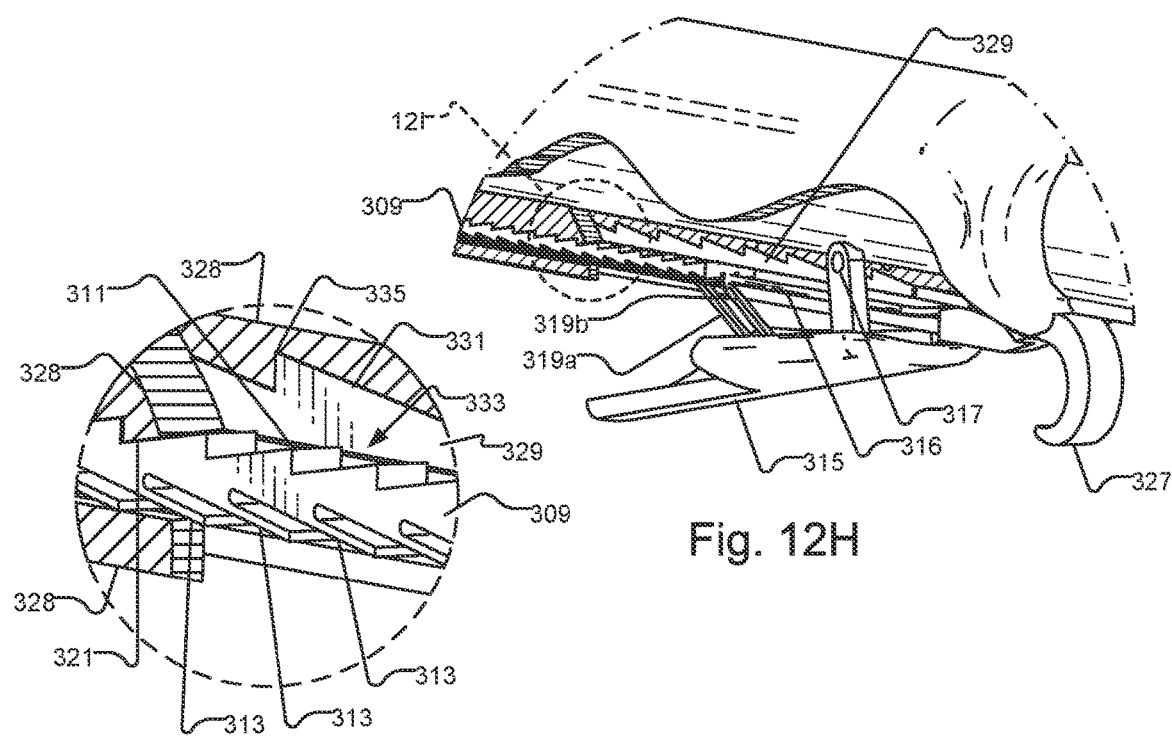
Fig. 12H
Fig. 12I
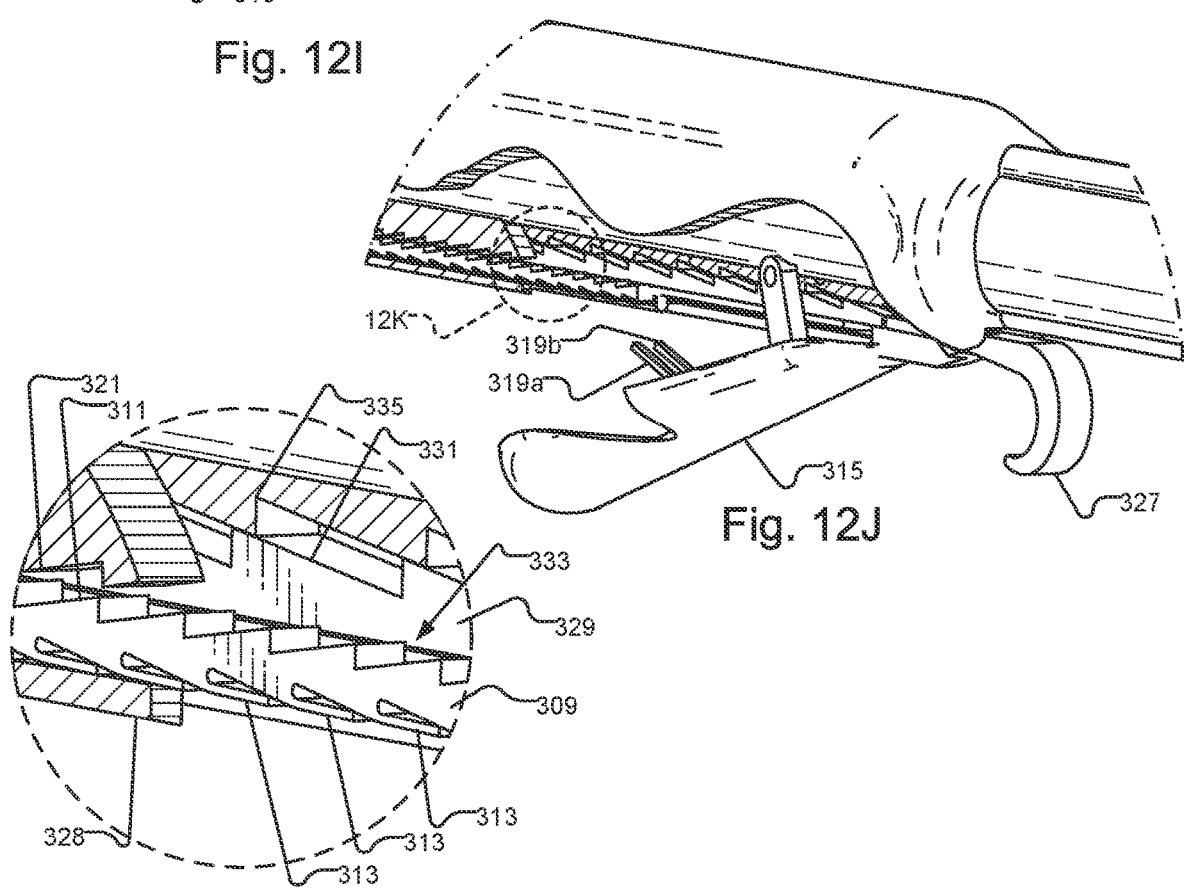
Fig. 12J
Fig. 12K

FLUID REMOVAL DEVICE

FIELD OF THE INVENTION

The present invention generally relates to methods and devices for removing fluids from a body during health care procedures. In particular, the present invention is directed to a steerable chest tube for removing fluids and air from a pleural space.

BACKGROUND

Chest injuries, whether blunt or penetrating, are common. When the chest wall or lung are injured, bleeding may occur into the pleural space between the chest wall and lung. Bleeding into this pleural space is termed a hemothorax. If left untreated, hemothorax can result in a limitation of lung function due to the reduction in potential space into which the lung can expand, thus reducing air entry into the lung. The emergent treatment of hemothorax involves placing a tube into the pleural space and applying an appropriate amount of negative pressure in order to drain the accumulated blood and/or other fluids. Insertion of the tube usually involves the creation of a small incision into the chest through the ribs and placing the tube into the pleural space. This treatment is referred to as tube thoracostomy. The procedure for removing air from the pleural space (as may be necessary in a case of pneumothorax) is essentially the same as for fluids, although, for purposes of clarity, descriptions herein will generally focus on fluid removal.

Currently, a typical chest tube for treating hemothorax and/or pneumothorax consists of a straight polyethylene or silicone tube with multiple holes placed in the end that is to be situated in the pleural space within the chest. After a small incision is made in the chest wall, insertion of this type of chest tube into the chest cavity is usually done in a "blind" fashion and the final location of the chest tube is not well known or controlled by the user. Since this type of chest tube is stiff and straight, the final location of the tip of the tube is usually in the mid-chest, either anteriorly or posteriorly. Since the pleural space is a continuous cavity, it is usually thought that a single tube is adequate to drain the fluid no matter where the tip is finally located.

However, in about 20% of these cases, the placement of a single undirected tube is insufficient to completely drain the fluid, which can result in a complication referred to as a retained hemothorax. This can be due to a final position of the tip of the tube that is not in direct contact with the accumulated blood. After a few days, the residual fluid in the pleural space may become congealed and fibrotic, which can result in permanent dysfunction of the lung without the performance of additional, more complex invasive procedures to remove the residual fluid. In the worst-case scenario, the residual fluid can become infected, resulting in an empyema, which is potentially life-threatening. Operative procedures to drain this residual fluid involve large incisions into the chest cavity or the insertion of thoracoscopes under general anesthesia to manually remove the clotted blood and fibrin. These additional procedures result in prolonged hospitalization and additional pain for the patient.

Suction applied to chest tubes during hemothorax treatment has been provided by hospital suction lines requiring extender tubing to connect chest tubes to "wall suction". This limits the mobility of patients, such as for being transported to tests and other therapies. Such suction is controlled by in-line valves to maintain appropriate pressures. Drained fluids are collected and contained in a plastic reservoir that hangs on the bedside. Monitoring of fluid output requires daily measurement of reservoir volumes and can be difficult to accurately estimate. Further, any infusion of materials into the pleural space during hemothorax treatment requires manual flushing, which involves a potentially dangerous disconnection of the chest tube from the collection device.

In order to better drain or remove fluid for treatment of hemothorax, there is a need for a steerable chest tube that can be directed into pleural locations where fluid may tend to accumulate. In addition, an extendable tubing system for instillation of anticoagulants and thrombolytics into the pleural space can be included with the steerable chest tube to further facilitate fluid removal and thereby limit the development of retained hemothorax. Pain relieving local anesthetic can also be infused through these extended tubes. In addition, a portable suction/infusion device attached to the chest tube would allow for continuous or as needed suction as well as continuous or as needed infusion of anticoagulants and other medications into the pleural space. Integrated control mechanisms for the suction and infusion functions would allow the coordination of those functions to best enhance the effects of the infusion and suction.

SUMMARY OF THE DISCLOSURE

In an exemplary embodiment, a device for removing fluid from pleural space is provided that includes a chest tube with a proximal end, a distal end, a lumen running through from the proximal end to the distal end, and a handle near the proximal end, wherein the chest tube has a slight resting curve. A first channel runs along a greater curvature of the resting curve of the chest tube, the first channel containing one or more cannulas with proximal ends and distal ends, wherein the distal ends of the plurality of cannulas can be extended beyond the first channel at the distal end of the chest tube and the proximal ends extend beyond the first channel near the proximal end of the chest tube. A second channel runs along a lesser curvature of the resting curve of the chest tube, the first channel containing a pull line with a distal end and a proximal end, wherein the distal end of the pull line is attached to the chest tube near the distal end of the chest tube such that when a force is applied to the pull line in a proximal direction the curve of the chest tube is increased. A tension assembly is included for applying force in the proximal direction to the pull line and for holding the pull line in place. A cannula extender assembly is included for extending the one or more cannulas beyond the first channel at the distal end of the chest tube and preventing the extended one or more cannulas from withdrawing, wherein the cannula extender assembly maintains sterility.

Additionally or alternatively, the cannula extender assembly includes a tab on the handle, the tab connected to an advancement member, the advancement member being secured to the one or more cannulas, wherein the handle includes a groove designed and configured to allow the tab to slide distally about 3-5 centimeters such that sliding the tab distally in the groove advances the distal ends of the one or more cannulas about 3-5 centimeters beyond the distal end of the chest tube.

Additionally or alternatively, the advancement member includes an O-ring designed and configured to maintain a seal between the advancement member and the first channel.

Additionally or alternatively, the cannula extender assembly further includes a stop, the stop designed and configured to prevent the advancement member from sliding in a proximal direction.

Additionally or alternatively, the stop includes a release.

Additionally or alternatively, the tension assembly includes a gripping device on the proximal end of the pull line, a plurality of evenly spaced beads attached to the pull line, and a V-lock attached to the tube, the V-lock designed and configured to prevent a selected one of the plurality of beads placed in the V-lock from moving distally when tension is on the pull line.

Additionally or alternatively, the tension assembly includes a gripping device attached to the proximal end of the pull line, a plurality of evenly spaced beads attached to the pull line, and a groove in the handle, wherein the groove includes a plurality of evenly spaced divots, each divot designed and configured to accept a one of the plurality of beads, wherein placement of at least a portion of the plurality of beads in a respective ones of the plurality of divots prevents the portion of the plurality of divots from moving distally when tension is on the pull line.

Additionally or alternatively, the tension assembly includes a first series of teeth on the handle, a second series of teeth on the handle, a lever hingeably attached to the handle, an advancing bar pivotably attached to the lever, a linear ratchet with a proximal end and a distal end, wherein the distal end is attached to the proximal end of the pull line, wherein the linear ratchet includes a plurality of teeth designed and configured to engage with the first series of teeth of the handle and a plurality of bias legs opposite the plurality of teeth of the linear ratchet, and a release member including a gripping portion extending out from the handle, a toothed portion designed and configured to slidably engage with the second series of teeth on the handle, and a flat portion designed and configured to engage the plurality of teeth of the linear ratchet. When the lever is compressed toward the handle, the advancing bar engages a one of the bias legs, thereby moving the linear ratchet proximally a distance such that each compression of the lever results in the pull line being pulled proximally the distance and the linear ratchet is prevented from moving distally by the engagement of the plurality of teeth of the linear ratchet with the first series of teeth of the handle, and when the gripping portion of the release member is moved distally, the toothed portion of the release member slides away from the second series of teeth of the handle, thereby causing the flat portion of the release member to apply force on the plurality of teeth of the linear ratchet, which compresses the bias legs and allows the portion of the plurality of teeth engaged with the first series of teeth of the handle to move freely with respect to the handle such that the pull line moves freely distally.

Additionally or alternatively, the tension assembly includes a retraction member attached to the proximal end of the pull line, the retraction member having a length approximately equal to a distance the pull line will be retracted to place the chest tube in a maximum curvature and including a grip to enable manipulation of the retraction member by a user's hand, and a support attached to the handle, the support including an opening configured to receive the retraction member and having a closed position and an open position, wherein in the closed position the support prevents the retraction member from moving in the proximal or the distal direction, wherein in the open position the support allows the retraction member to slide in both the proximal and the distal direction, and wherein in both the open position and the closed position, the grip is accessible to the user's hand.

Additionally or alternatively, the retraction member includes a plurality of markings and the support includes an indicator that is aligned with a one of the plurality of markings, the indicated marking being associated with an extent of retraction of the retraction member.

Additionally or alternatively, the plurality of markings include representations of the chest tube that represent approximate curvatures assumed by the chest tube based on the extent of retraction of the retraction member.

Additionally or alternatively, the tension assembly includes a spool attached to the handle and including a plurality of teeth, wherein the distal end of the pull line is attached to the spool, wherein winding the spool in a first direction retracts the pull line in the proximal direction, and wherein winding the spool in a second direction allows any retracted pull line to return in the distal direction, and a pawl configured to engage with the plurality of teeth of the spool, wherein when the pawl is engaged with a one of the plurality of teeth of the spool the spool is prevented from turning in the second direction while still being free to turn in the first direction.

Additionally or alternatively, the spool tension assembly further includes a display on the handle that indicates a curvature status of the chest tube, the displayed curvature status being linked to a number of turns of the spool in the first direction from a default position.

Additionally or alternatively, the display includes representations of the chest tube in an approximate curvature the chest tube will assume given the number of turns of the spool in the first direction from the default position.

Additionally or alternatively, the device for removing fluid includes a suction device connected to the chest tube, the suction device including a suction source connected to a proximal end of the lumen, an infusion source connected to the proximal ends of the one or more cannulas, a reservoir for holding fluid drained from the lumen, a second reservoir for holding infusion fluid, and a battery.

Additionally or alternatively, the chest tube includes an etched metal component near the distal end of the chest tube.

Additionally or alternatively, the chest tube includes a longitudinal radiopaque marking line on a portion of the chest tube.

Additionally or alternatively, the distal end of the chest tube includes a tip, the tip having a plurality of lobes extending distally from the chest tube and connected by a plurality of bridges at an approximate midpoint of the lobes, thereby forming holes between the lobes and a scalloped profile of a distal end of the tip.

Additionally or alternatively, the chest tube includes a plurality of makings to indicate distance from the distal end of the chest tube.

Additionally or alternatively, the chest tube includes a distal portion and a proximal portion, and wherein the proximal portion is less flexible than the distal portion such that the distal portion will tend to assume a greater curvature when force is applied to the pull line while the proximal portion retains a substantially similar configuration.

Additionally or alternatively, the distal portion of the chest tube has a length approximately a distance that the chest tube will be inserted into a patient's chest.

Additionally or alternatively, the device for removing fluid further includes a sewing collar around the chest tube, the sewing collar including a compression ring and a plurality of flanges, wherein each of the plurality of flanges includes a hole to hold sutures to secure a placement of the chest tube to skin of a chest wall of a patient.

In another embodiment, a fluid removal system is provided that includes a tube with a proximal end and a distal end, wherein the tube has a slight resting curve and is open on the proximal end and the distal end and includes a plurality of holes near the distal end. The tube also has a first channel along a greater curvature of the resting curve of the tube containing a plurality of cannulas with proximal ends and distal ends, wherein the distal ends of the plurality of cannulas can be extended beyond the first channel at the distal end of the tube. In addition, the tube has a second channel along a lesser curvature of the resting curve of the tube containing a pull line with a distal end and a proximal end, wherein the distal end of the line is attached to the tube near the distal end of the tube and wherein a force applied to the pull line in a proximal direction causes the curve of the tube to reversibly increase. A locking mechanism is attached to the tube, the locking mechanism reversibly securing the pull line in place such that, when tension is placed on the pull line such that the curve of the tube is increased and the pull line is secured in the locking mechanism, the increased curve of the tube is maintained.

Additionally or alternatively, the fluid removal system may include a suction device connected to the tube, the suction device including a suction source connected to the proximal end of the tube, an infusion source connected to the proximal ends of the plurality of cannulas, a reservoir for holding fluid drained from the tube, a second reservoir for holding infusion fluid, and a battery for a backup power source.

Additionally or alternatively, the fluid removal system includes an etched metal component near the distal end of the tube.

Additionally or alternatively, the fluid removal system includes a longitudinal radiopaque marking line on a portion of the tube.

Additionally or alternatively, the distal end of the tube includes a tip, the tip having a plurality of lobes extending distally from the tube and connected by a plurality of bridges at an approximate midpoint of the lobes, thereby forming holes between the lobes and a scalloped profile of a distal end of the tip.

Additionally or alternatively, the fluid removal system includes a plurality of makings on the tube to indicate distance from the distal end of the tube.

Additionally or alternatively, the tube includes a distal portion and a proximal portion, and wherein the proximal portion is less flexible than the distal portion such that the distal portion will tend to assume a greater curvature when force is applied to the pull line while the proximal portion retains a substantially similar configuration.

Additionally or alternatively, the distal portion of the tube has a length approximately a distance that the tube will be inserted into a patient's chest.

Additionally or alternatively, the fluid removal system includes a sewing collar around the tube, the sewing collar including a compression ring and a plurality of flanges, wherein each of the plurality of flanges includes a hole to hold sutures to secure a placement of the tube to skin of a chest wall of a patient.

Additionally or alternatively, the fluid removal device includes a handle, the handle including a tab connected to an advancement member, the advancement member being secured to the plurality of cannulas, wherein the handle includes a groove designed and configured to allow the tab to slide distally about 3-5 centimeters such that sliding the tab distally in the groove advances the distal ends of the plurality of cannulas about 3-5 centimeters beyond the distal end of the tube.

Additionally or alternatively, the advancement member includes an O-ring designed and configured to maintain a seal between the advancement member and the first channel.

Additionally or alternatively, the advancement member includes a stop, the stop designed and configured to prevent the advancement member from sliding in a proximal direction.

Additionally or alternatively, the stop includes a release.

Additionally or alternatively, the locking mechanism includes a gripping device on the proximal end of the pull line, a plurality of evenly spaced beads attached to the pull line, and a V-lock attached to the tube, the V-lock designed and configured to prevent a selected one of the plurality of beads placed in the V-lock from moving distally when tension is on the pull line.

Additionally or alternatively, the locking mechanism includes a handle on the tube, a gripping device attached to the proximal end of the pull line, a plurality of evenly spaced beads attached to the pull line, and a groove in the handle, wherein the groove includes a plurality of evenly spaced divots, each divot designed and configured to accept a one of the plurality of beads, wherein placement of at least a portion of the plurality of beads in a respective ones of the plurality of divots prevents the portion of the plurality of divots from moving distally when tension is on the pull line.

Additionally or alternatively, the locking mechanism includes a handle on the tube, a first series of teeth on the handle, a second series of teeth on the handle; a lever hingeably attached to the handle, an advancing bar pivotably attached to the lever, a linear ratchet with a proximal end and a distal end, wherein the distal end is attached to the proximal end of the pull line, wherein the linear ratchet includes a plurality of teeth designed and configured to engage with the first series of teeth of the handle and a plurality of bias legs opposite the plurality of teeth of the linear ratchet, and a release member including a gripping portion extending out from the handle, a toothed portion designed and configured to slidably engage with the second series of teeth on the handle, and a flat portion designed and configured to engage the plurality of teeth of the linear ratchet. When the lever is compressed toward the handle, the advancing bar engages a one of the bias legs, thereby moving the linear ratchet proximally a distance such that each compression of the lever results in the pull line being pulled proximally the distance and the linear ratchet is prevented from moving distally by the engagement of the plurality of teeth of the linear ratchet with the first series of teeth of the handle, and when the gripping portion of the release member is moved distally, the toothed portion of the release member slides away from the second series of teeth of the handle, thereby causing the flat portion of the release member to apply force on the plurality of teeth of the linear ratchet, which compresses the bias legs and allows the portion of the plurality of teeth engaged with the first series of teeth of the handle to move freely with respect to the handle such that the pull line moves freely distally.

Additionally or alternatively, the locking mechanism includes a handle on the tube, a retraction member attached to the proximal end of the pull line, the retraction member having a length approximately equal to a distance the pull line will be retracted to place the tube in a maximum curvature and including a plurality of grips to enable manipulation of the retraction member by a user's hand, and a retraction member support attached to the handle, the support including an opening configured to receive the retraction member and having a closed position and an open position, wherein in the closed position the support prevents the retraction member from moving in the proximal or the distal direction and wherein in the open position the support allows the retraction member to slide in both the proximal and the distal direction.

Additionally or alternatively, the retraction member includes a plurality of markings and the support includes an indicator that is aligned with a one of the plurality of markings, the one indicated marking being associated with an extent of retraction of the retraction member.

Additionally or alternatively, the plurality of markings include representations of the tube that represent approximate curvatures assumed by the tube based on the extent of retraction of the retraction member.

Additionally or alternatively, the locking mechanism includes a handle on the tube, a spool attached to the handle and including a plurality of teeth, wherein the distal end of the pull line is attached to the spool, wherein winding the spool in a first direction retracts the pull line in the proximal direction, and wherein winding the spool in a second direction allows any retracted pull line to return in the distal direction, and a pawl configured to engage with the plurality of teeth of the spool, wherein when the pawl is engaged with a one of the plurality of teeth of the spool the spool is prevented from turning in the second direction while still being free to turn in the first direction.

Additionally or alternatively, the spool locking mechanism further includes a display on the handle that indicates a curvature status of the tube, the displayed curvature status being linked to a number of turns of the spool in the first direction from a default position.

Additionally or alternatively, the second channel includes one or more openings.

In another embodiment, a chest tube assembly is provided that has a tube with a proximal end, a distal end, a lumen running through from the proximal end to the distal end, and a handle near the proximal end, wherein the tube has a resting curve, a pull line with a distal end and a proximal end, wherein the distal end of the pull line is attached to the tube near the distal end of the chest tube such that when a force is applied to the pull line in a proximal direction the curve of the tube is increased, and a tension assembly for applying force in the proximal direction to the pull line and for holding the pull line in place.

Additionally or alternatively, the tube has a sidewall with a ventral portion, a dorsal portion, a first lateral portion and a second lateral portion opposite the first lateral portion, and wherein for at least a portion of the sidewall of the first lateral portion and the second lateral portion are thicker than the ventral portion and the dorsal portion.

Additionally or alternatively, the first lateral portion and the second lateral portion have similar thicknesses and the ventral portion and the lateral portion have similar but smaller thicknesses.

Additionally or alternatively, the tension assembly includes a gripping device on the proximal end of the pull line, a plurality of evenly spaced beads attached to the pull line, and a V-lock attached to the tube, the V-lock designed and configured to prevent a selected one of the plurality of beads placed in the V-lock from moving distally when tension is on the pull line.

Additionally or alternatively, the tension assembly includes a handle, a gripping device attached to the proximal end of the pull line, a plurality of evenly spaced beads attached to the pull line, and a groove in the handle, wherein the groove includes a plurality of evenly spaced divots, each divot designed and configured to accept a one of the plurality of beads, wherein placement of at least a portion of the plurality of beads in a respective ones of the plurality of divots prevents the portion of the plurality of divots from moving distally when tension is on the pull line.

Additionally or alternatively, the tension assembly includes a handle, a first series of teeth on the handle, a second series of teeth on the handle, a lever hingeably attached to the handle, an advancing bar pivotably attached to the lever, a linear ratchet with a proximal end and a distal end, wherein the distal end is attached to the proximal end of the pull line, wherein the linear ratchet includes a plurality of teeth designed and configured to engage with the first series of teeth of the handle and a plurality of bias legs opposite the plurality of teeth of the linear ratchet, and a release member including a gripping portion extending out from the handle, a toothed portion designed and configured to slidably engage with the second series of teeth on the handle, and a flat portion designed and configured to engage the plurality of teeth of the linear ratchet, wherein when the lever is compressed toward the handle, the advancing bar engages a one of the bias legs, thereby moving the linear ratchet proximally a distance such that each compression of the lever results in the pull line being pulled proximally the distance and the linear ratchet is prevented from moving distally by the engagement of the plurality of teeth of the linear ratchet with the first series of teeth of the handle, and when the gripping portion of the release member is moved distally, the toothed portion of the release member slides away from the second series of teeth of the handle, thereby causing the flat portion of the release member to apply force on the plurality of teeth of the linear ratchet, which compresses the bias legs and allows the portion of the plurality of teeth engaged with the first series of teeth of the handle to move freely with respect to the handle such that the pull line moves freely distally.

Additionally or alternatively, the tension assembly includes a handle, a retraction member attached to the proximal end of the pull line, the retraction member having a length approximately equal to a distance the pull line will be retracted to place the chest tube in a maximum curvature and including a grip to enable manipulation of the retraction member by a user's hand, and a retraction member support attached to the handle, the support including an opening configured to receive the retraction member and having a closed position and an open position, wherein in the closed position the support prevents the retraction member from moving in the proximal or the distal direction, wherein in the open position the support allows the retraction member to slide in both the proximal and the distal direction, and wherein in both the open position and the closed position, the grip is accessible to the user's hand.

Additionally or alternatively, the retraction member includes a plurality of markings and the support includes an indicator that is aligned with a one of the plurality of markings, the indicated marking being associated with an extent of retraction of the retraction member.

Additionally or alternatively, the plurality of markings include representations of the chest tube that represent approximate curvatures assumed by the chest tube based on the extent of retraction of the retraction member.

Additionally or alternatively, the tension assembly includes a spool attached to the handle and including a plurality of teeth, wherein the distal end of the pull line is attached to the spool, wherein winding the spool in a first direction retracts the pull line in the proximal direction, and wherein winding the spool in a second direction allows any retracted pull line to return in the distal direction, and a pawl configured to engage with the plurality of teeth of the spool, wherein when the pawl is engaged with a one of the plurality of teeth of the spool the spool is prevented from turning in the second direction while still being free to turn in the first direction.

Additionally or alternatively, the spool tension assembly further includes a display on the handle that indicates a curvature status of the chest tube, the displayed curvature status being linked to a number of turns of the spool in the first direction from a default position.

Additionally or alternatively, the display includes representations of the chest tube in an approximate curvature the chest tube will assume given the number of turns of the spool in the first direction from the default position.

Additionally or alternatively, the distal end of the tube includes a tip, the tip having a plurality of lobes extending distally from the tube and connected by a plurality of bridges at an approximate midpoint of the lobes, thereby forming holes between the lobes and a scalloped profile of a distal end of the tip.

Additionally or alternatively, a plurality of makings are included on the tube to indicate distance from the distal end of the tube.

Additionally or alternatively, the tube includes a distal portion and a proximal portion, and wherein the proximal portion is less flexible than the distal portion such that the distal portion will tend to assume a greater curvature when force is applied to the pull line while the proximal portion retains a substantially similar configuration.

Additionally or alternatively, the distal portion of the tube has a length approximately a distance that the tube will be inserted into a patient's chest.

Additionally or alternatively, a sewing collar is included around the tube, the sewing collar including a compression ring and a plurality of flanges, wherein each of the plurality of flanges includes a hole to hold sutures to secure a placement of the chest tube assembly to skin of a chest wall of a patient.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 9A-9D show detail and cutaway views of a tension/locking mechanism of the steerable chest tube of FIG. 6A;

FIG. 10B is a detail, cutaway view of the cannula extender of FIG. 10A in a retracted position;

FIG. 10C is a detail view of a portion of FIG. 10B,

FIG. 10D is a detail, cutaway view of the cannula extender of FIG. 10A in an extended position;

FIGS. 12A-12K views of another tension/locking mechanism of the present invention;

DESCRIPTION OF THE DISCLOSURE

A steerable chest tube of the present invention allows for accurate placement of the distal end of the chest tube within the pleural space to facilitate more complete drainage of fluid from the pleural space during treatment of hemothorax. The degree of curvature of the chest tube can be increased or decreased while the distal end of the tube is within the pleural space. By increasing or decreasing the curve of the steerable chest tube in combination with controlled rotation and insertion distance, the distal end of the steerable chest tube can be positioned at almost any desired location within the pleural space. The insertion and placement distal end of the chest tube into a desired position can, without extensive training, be done "blindly" in emergency situations, such as may be encountered by combat medics. In other situations, where additional facilities are available, the location of the distal end of the tube within the pleural space can be verified or determined using ultrasound, magnetic detection, or other locating methods.

Controlled infusion of anticoagulants into the chest cavity early in hemothorax treatment may help prevent early coagulation of retained blood in the chest and so further facilitate more complete drainage of fluid from the pleural space. The controlled irrigation of anticoagulants can be delivered via cannulas that can be extended beyond the end of the steerable chest tube to directly infuse anticoagulants into any potential clots in the pleural space. In addition, later in the course of treatment of retained hemothorax, thrombolytic drugs can be infused through the same cannulas to dissolve clot which will then facilitate drainage. Throughout the course of treatment, local anesthetics can be infused through the same cannulas to alleviate pain from chest tube placement or antecedent injury.

A portable suction device can be attached to the steerable chest tube to provide continuous or as needed suction for chest tube aspiration. In addition, the portable suction device can provide for accurate effluent measurement and for continuous or as needed infusion of appropriate treatment medications into the pleural space.

In this way, a more complete removal of fluid that accumulates in pleural space as the result of a chest injury or pleural disease can be achieved, which would be an improvement in hemothorax and pleural effusion treatment and thus avoid additional expensive and painful procedures.

Figure 1A:
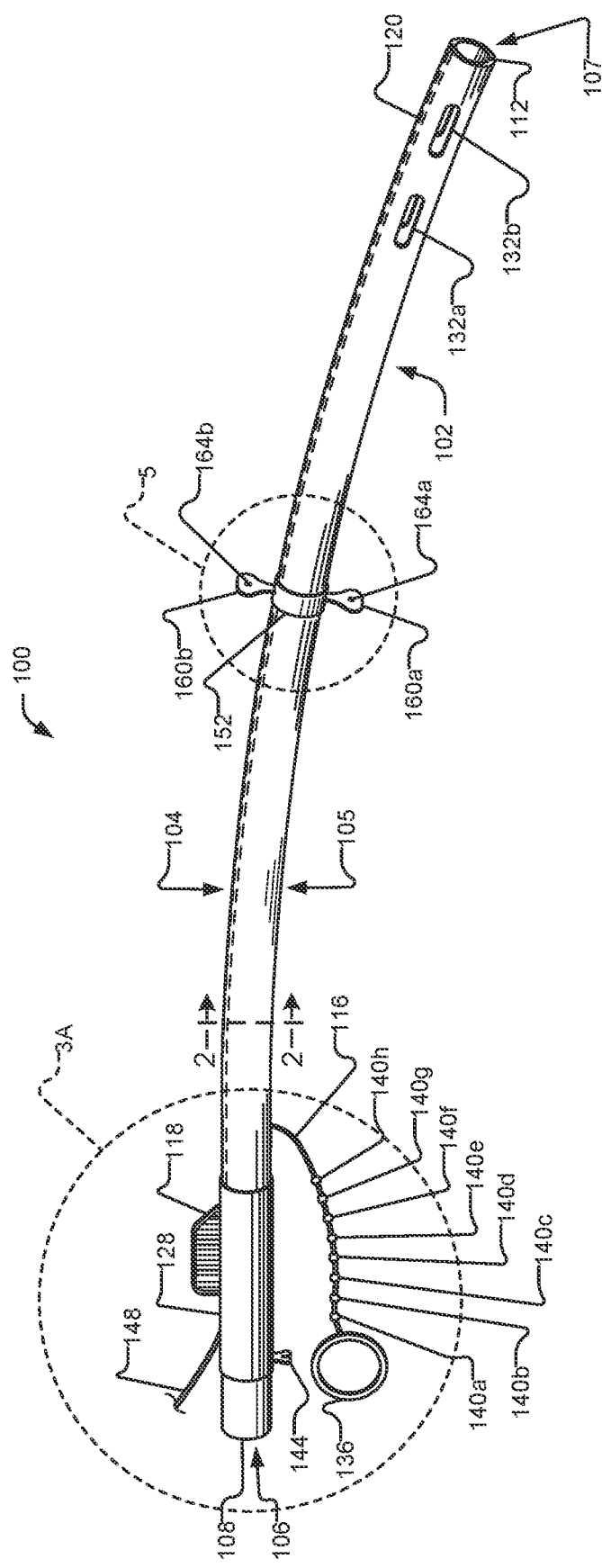
FIG. 1A is a perspective view of a steerable chest tube in accordance with an embodiment of the present invention.
Figure 1B:
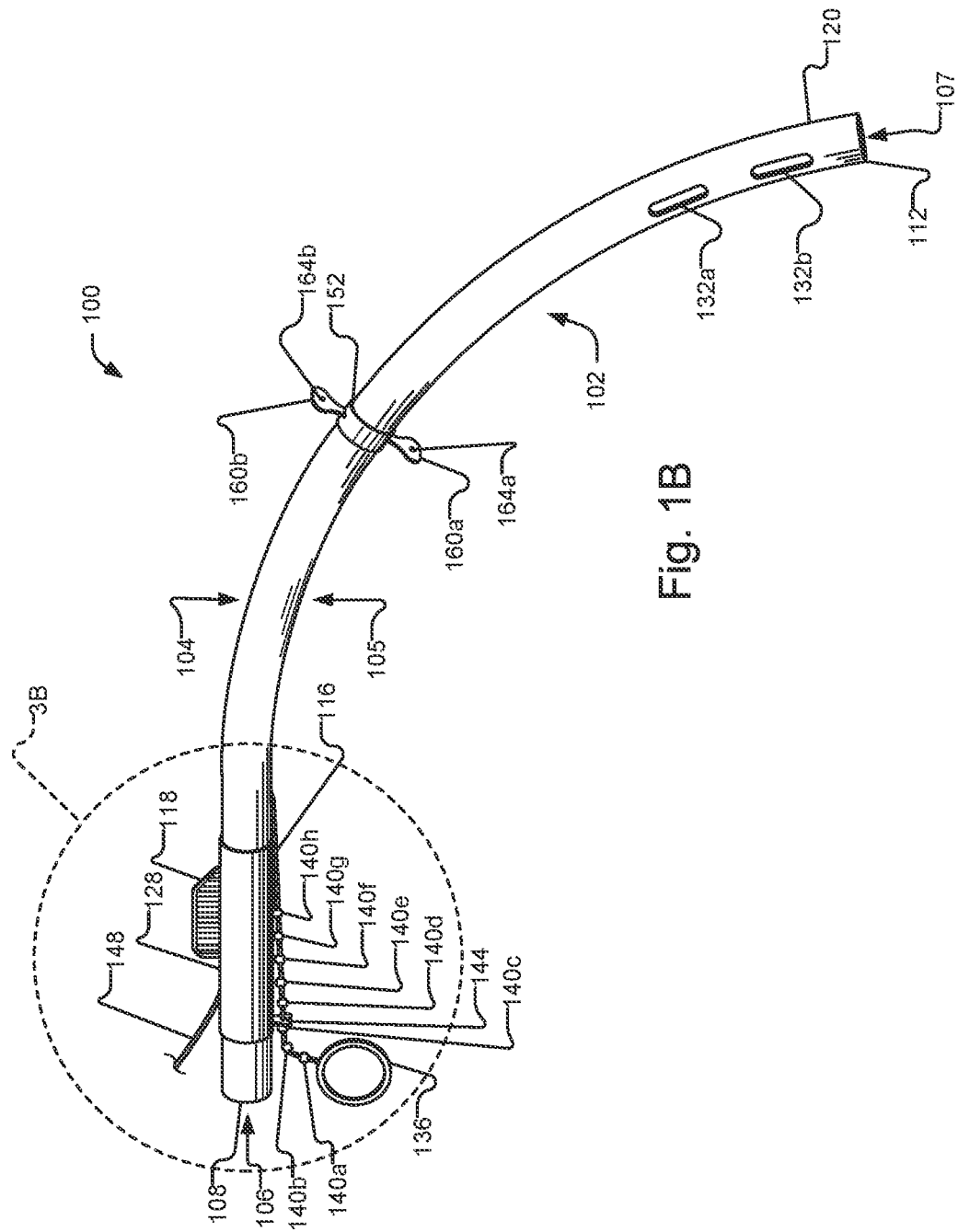
FIG. 1B is a perspective view of the steerable chest tube of FIG. 1A in another conformation.
Figure 2:
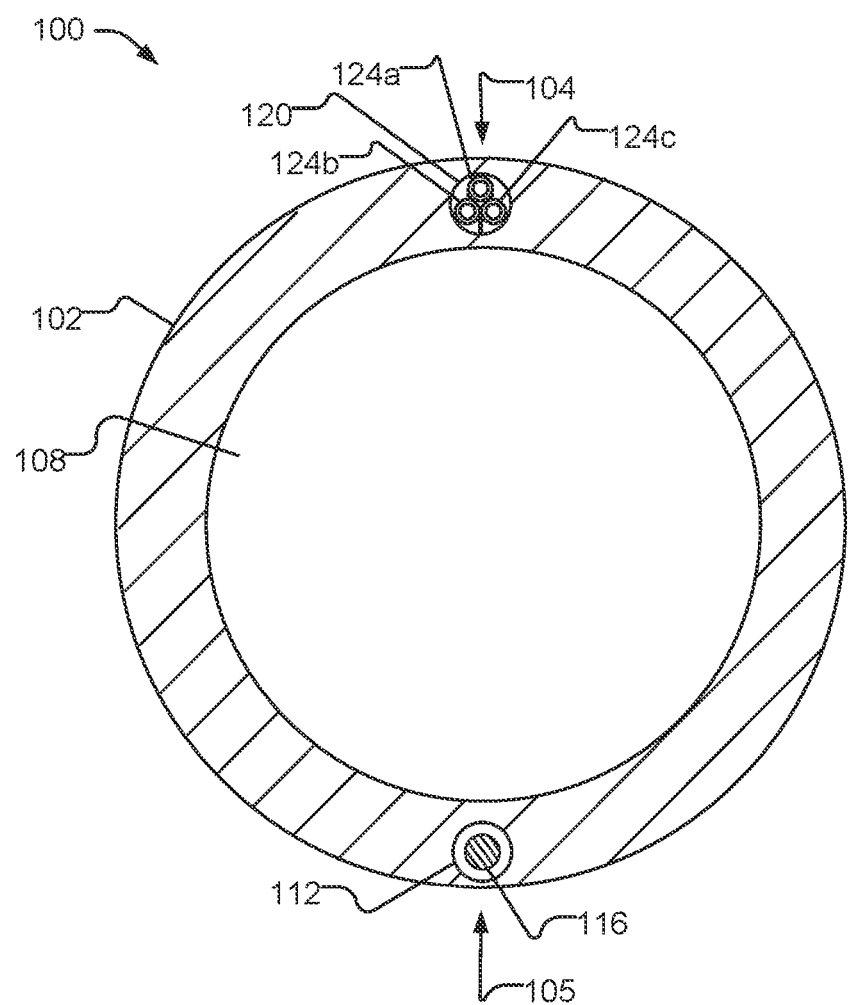
FIG. 2 is a cross-sectional view of the steerable chest tube of FIG. 1A.

With reference now to FIGS. 1A, 1B, and 2, a steerable chest tube assembly 100 is shown according to an embodiment of the present disclosure. Steerable chest tube assembly 100 includes a tube 102, which has a greater curvature 104, a lesser curvature 105, a proximal end 106, and a distal end 107. Proximal end 106 can be connected to a source of suction when needed, while distal end 107 is inserted into the pleural space of the chest cavity during a hemothorax treatment. As can be seen more clearly in FIG. 2, tube 102 also includes an inner lumen 108 through which fluids are drained, a lesser curvature channel 112 for containing a pull wire or line 116 that allows the curvature of tube 102 to be adjusted at the time of insertion, and a greater curvature channel 120 for containing one or more extendable cannulas 124 (e.g., 124*a*-124*c*) that can deliver medications into the pleural space. In addition, chest tube assembly 100 may include a handle 128, which encompasses tube 102 near proximal end 106 and includes mechanisms for extending cannulas 124 and for controlling tension on line 116 in order to adjust the curvature of tube 102. (These mechanisms are discussed in more detail below).

Tube 102 may be made of any suitable material, such as polyethylene or silicone, and in a preferred embodiment has an outer diameter between about 9-12 millimeters. Tube 102 is open on both proximal end 106 and distal end 107 to allow fluid and air to be drained from the pleural space through inner lumen 108. Openings 132 (e.g., 132*a*-132*b*) near distal end 107 of tube 102 further facilitate fluid drainage from the pleural space.

In a resting position, as shown in FIG. 1A, tube 102 may have a slight curve, and is flexible enough to be bent into an increased curve with a memory that would, absent tension bending tube 102 into an increased curve, tend toward assuming the original slight curve.

Lesser curvature channel 112 is embedded within tube 102 (as can be seen in FIG. 2) along lesser curvature 105. Pull line 116 is a flexible line, thread, string or wire, which can be polyethylene or other suitable material, that can pass through lesser curvature channel 112 and is used to adjust the curve of chest tube assembly 100. Pull line 116 is firmly attached at or near distal end 107 of tube 102 and runs through lesser curvature channel 112 until exiting approximately between a midpoint and proximal end 106 of tube 102, preferably at or near handle 128. A ring 136 or other suitable device for gripping is preferably included at or near a proximal end of pull line 116. Applying force on pull line 116 toward proximal end 106 causes tube 102 to bend, increasing the curve continuously until a desired curve is attained. FIG. 1B shows chest tube assembly 100 in an increased curvature configuration. Lessening tension on pull line 116 allows the curve of tube 102 to decrease back toward the original slight curve. Pull line 116 and the flexibility of tube 102 thus allows the curvature of chest tube assembly 100 to be adjusted while distal end 107 is inserted in the pleural space.

Figure 3A:
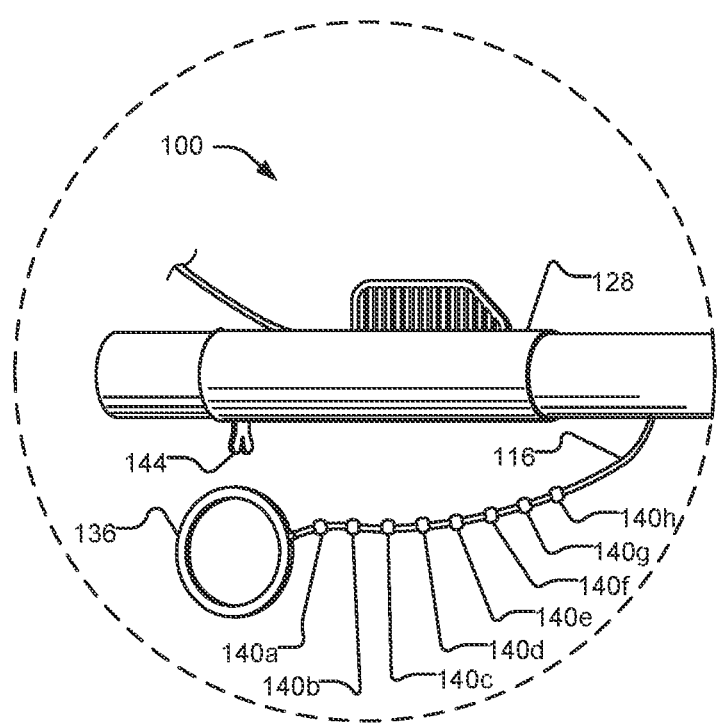
FIG. 3A is a detail view of a tension/locking mechanism for the steerable chest tube of FIG. 1A.
Figure 3B:
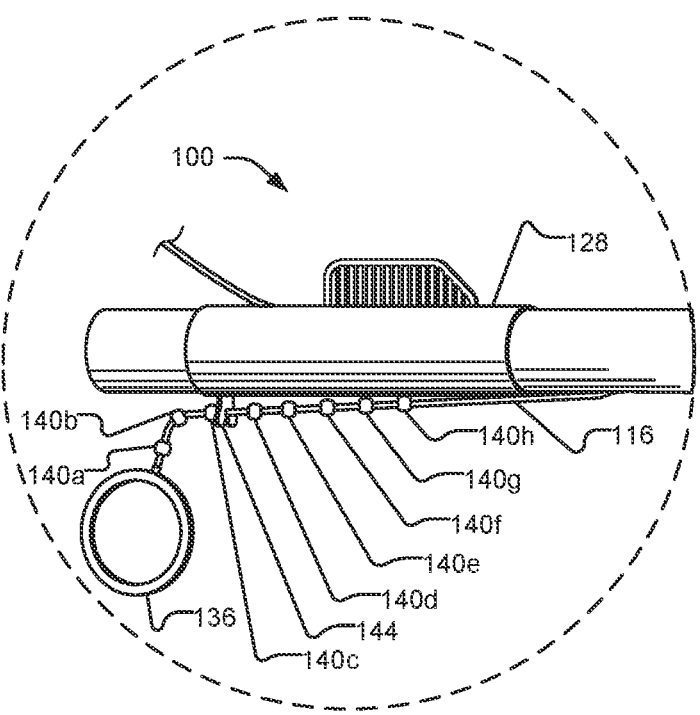
FIG. 3B shows the tension/locking mechanism of FIG. 3A in another conformation.

In order to lock chest tube assembly 100 into a desired degree of curvature, any suitable mechanism can be used to hold pull line 116 in place. In one embodiment, shown in FIGS. 3A and 3B, several beads 140 (e.g., 140*a*-140*h*) are attached to pull line 116 about a centimeter apart on a portion of pull line 116 that is external to lesser curvature channel 112. A V-lock 144 is included on handle 128, and by pulling on ring 136 pull line 116 can be positioned into V-lock 144 such that the nearest bead 140 on the proximal side of V-lock 144 (in FIG. 3B, this is bead 140*c*) will be stopped by V-lock 144 and thus keep pull line 116 from sliding any further distally upon release of tension on pull line 116. In this way the curvature of tube 102 created by placing tension on pull line 116 can be maintained without the need for a user to continuously apply tension (i.e., hold onto ring 136). With several closely spaced beads 140 along pull line 116, tube 102 can be locked in many different degrees of curvature, with the particular bead 140 that is secured in V-lock 144 being approximately associated with an amount of curvature. In addition, an optional mechanism may be included for preventing a bead from accidentally slipping out of V-lock 144, so that if chest tube assembly is bumped or jostled after insertion and locking of curvature, pull line 116 will not move freely.

Cannulas 124 are included in greater curvature channel 120 and can move through greater curvature channel 120. Cannulas 124 may be braided together to form a braided bundle or cannula assembly 148, which may be reinforced with a fine wire (not shown) to impart stiffness to facilitate movement through greater curvature channel 120. Cannulas 124 can be used to deliver medications into the pleural space.

Figure 4:
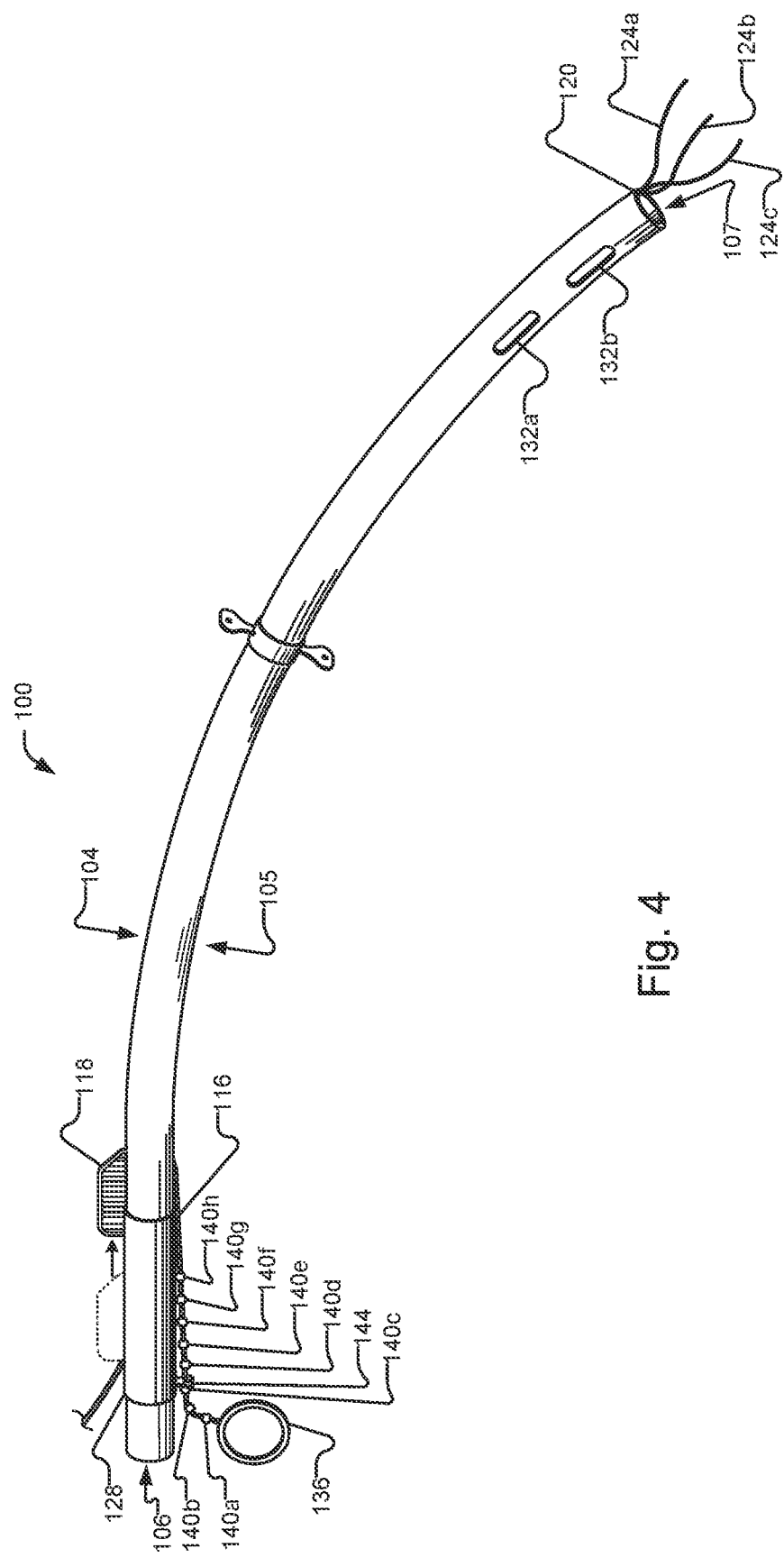
FIG. 4 shows a cannula extender in accordance with an embodiment of the present invention.

A push tab 118 attached on or near handle 128 engages near a proximal end of greater curvature channel 120. Push tab 118 engage cannula assembly 148 and when pushed distally will extend cannulas out of greater curvature channel 120 and into the pleural space, as shown in FIG. 4. Cannulas 124 are connected at their proximal ends to an infusion device (discussed further below). As noted, twisting cannula assembly 148 several times will cause cannulas 124 to separate and thus be distributed into the pleural space so that the delivery of anticoagulants, for example, will be more evenly dispersed.

Distal end 107 of tube 102 may include an etched metal component (not shown) configured to scatter ultrasound waves, which facilitates localization of distal end 107 of tube 102 within the pleural space by the use of transcutaneous ultrasound, when available. Alternatively, distal end 120 of tube 102 may include a small embedded magnet allowing detection of tube location by a portable magnetometer placed on the skin of the thorax of the patient.

Figure 5:
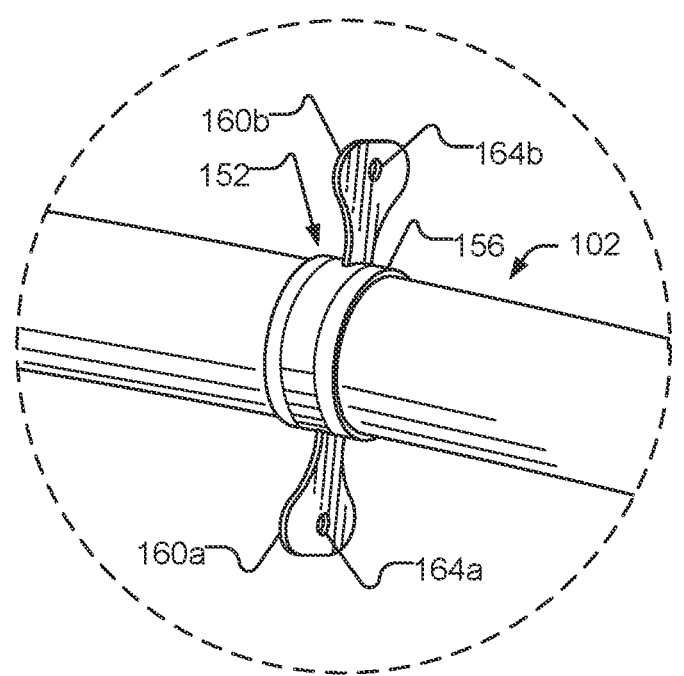
FIG. 5 is a detail view of a sewing collar for the steerable chest tube of FIG. 1A.

Turning to FIG. 5, a sewing collar 152 may be included on tube 102 that encircles a mid-portion of tube 102. Collar 152 is movable along tube 102 but can be secured anywhere along tube 102 by a suitable mechanism, preferably an adjustable friction or compression ring 156. Extending from collar 152 are flanges or wings 160 (e.g., 160*a*, 160*b*) with notches or holes 164 (e.g., 164*a*, 164*b*) to hold sutures to secure the placement of chest tube assembly 100 to the skin of the chest wall in order to hold chest tube assembly 100 in place once distal end 107 is in a desired location in the pleural space.

Figure 6A:
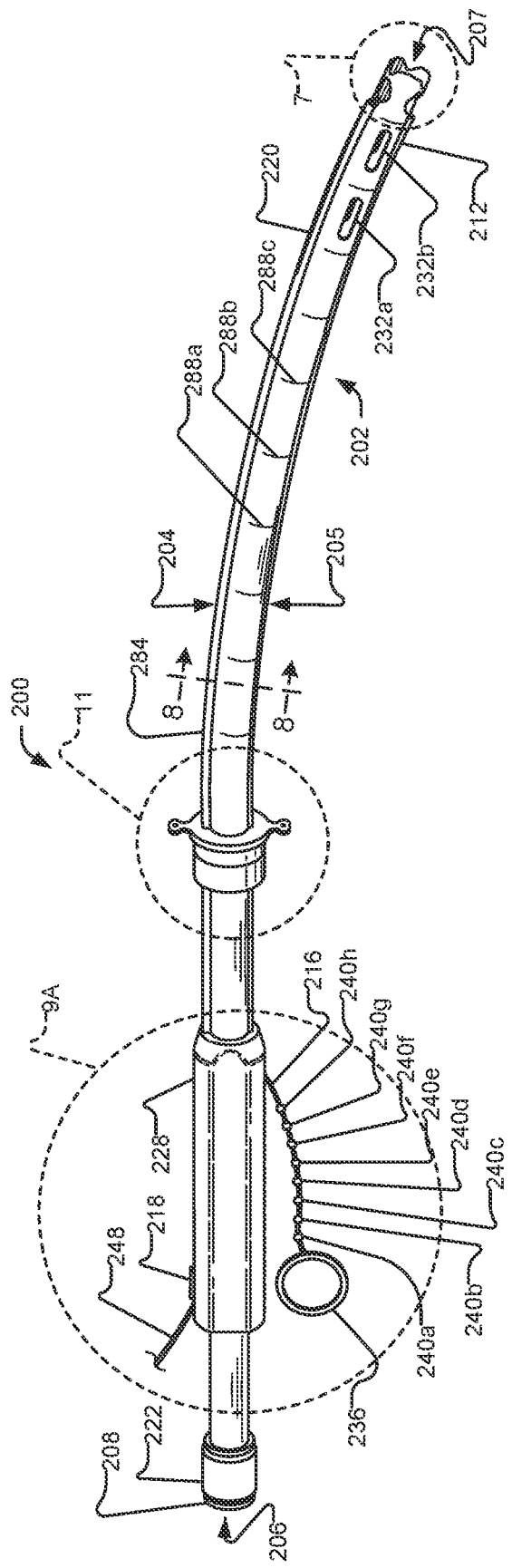
FIG. 6A is a perspective view of another embodiment of a steerable chest tube in accordance with another embodiment of the present invention.
Figure 6B:
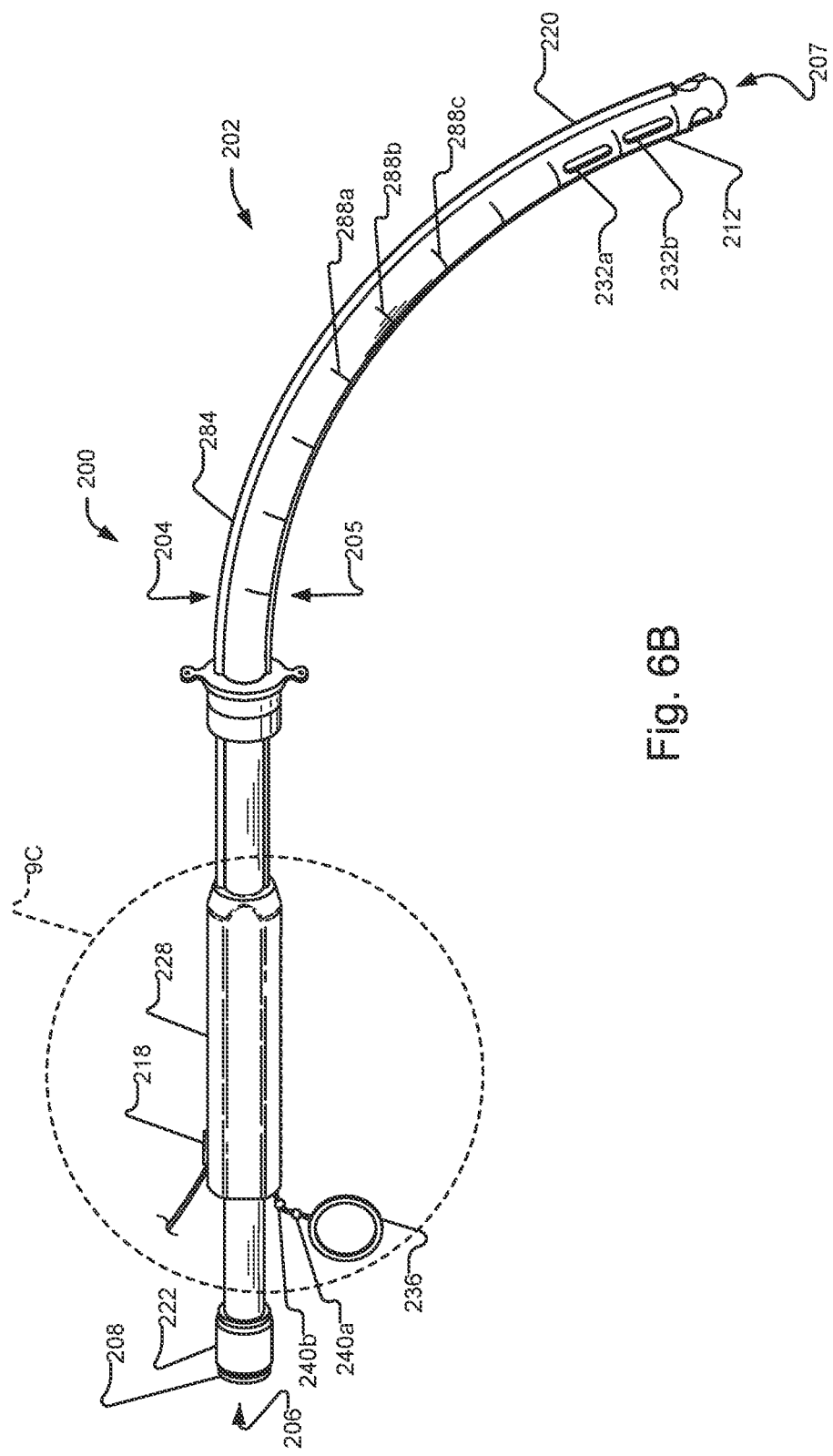
FIG. 6B is a perspective view of the steerable chest tube of FIG. 6A in another conformation.

In another embodiment, as shown in FIGS. 6A-6B, a steerable chest tube assembly 200 includes a tube 202 with a greater curvature 204, a lesser curvature 205, a proximal end 206, and a distal end 207. Proximal end 206 can be connected to a source of suction when needed, while distal end 207 is inserted into the pleural space of the chest cavity during a hemothorax treatment. As can be seen more clearly in FIG. 8, tube 202 also includes an inner lumen 208 through which fluids are drained, a lesser curvature channel 212 for containing a pull wire or line 216 that allows the curvature of tube 202 to be adjusted at the time of insertion, and a greater curvature channel 220 for containing one or more extendable cannulas 224 (e.g., 224*a*-224*c*) that can deliver medications into the pleural space. Preferably, lesser curvature channel 212 will be closed at a distal end and unperforated along its length that will be within a patient's chest. Pull line 216 is attached near or at a distal end of lesser curvature channel 212 by any suitable technique, such as gluing, crimping, melting, or fusing. In addition, chest tube assembly 200 may include a handle 228, which encompasses or is otherwise attached to tube 202 near proximal end 206 and includes mechanisms for extending cannulas 224 and for controlling tension on line 216 in order to adjust the curvature of tube 202. (These mechanisms are discussed in more detail below.)

Tube 202 may be made of any suitable material, such as polyethylene or silicone, and in a preferred embodiment has an outer diameter between about 9-12 millimeters. Tube 202 is open on both proximal end 206 and distal end 207 to allow fluid and air to be drained from the pleural space through inner lumen 208. Openings 232 (e.g., 232a-232b) near distal end 207 of tube 202 further facilitate fluid drainage from the pleural space. A connector 222, such as a push-to-connect fitting, may be used to connect proximal end 206 of tube 202 to tubing of a suction device or pump.

Figure 7:
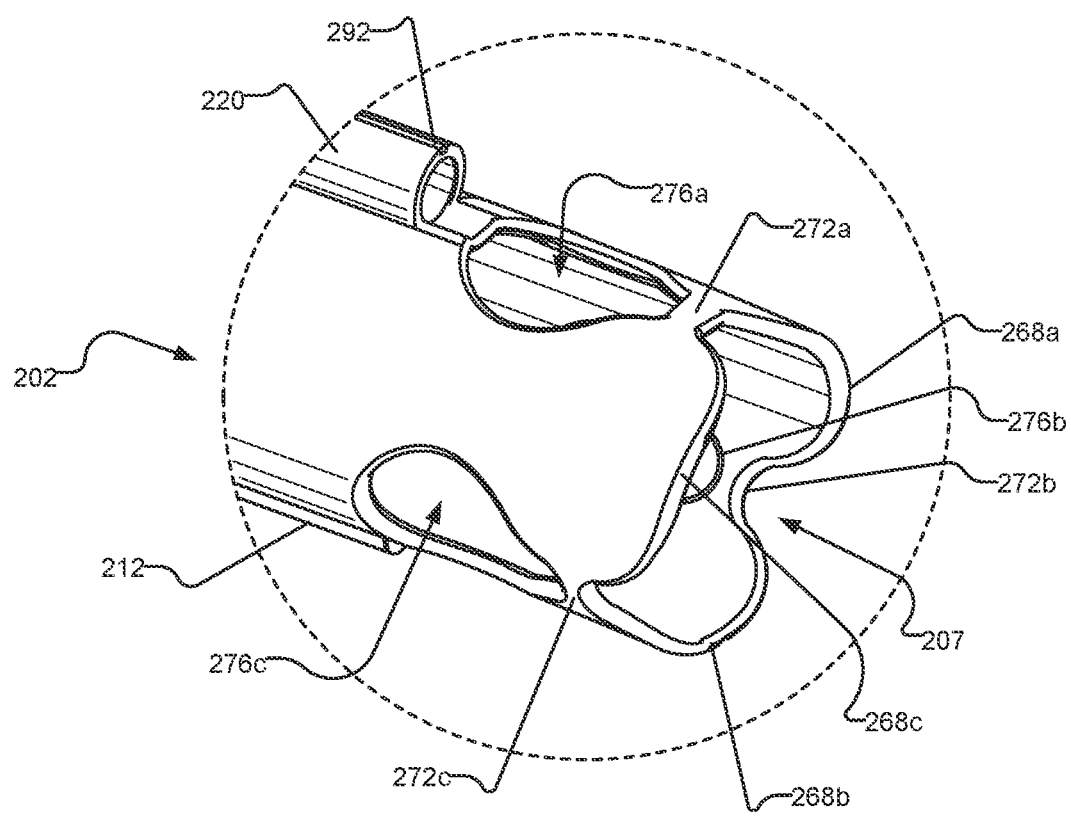
FIG. 7 is a detail perspective view of the distal end of the steerable chest tube of FIG. 6A.

Further, distal end 207, as shown in detail in FIG. 7, is configured to allow for increased area for the application of suction as well to reduce the risk of distal end 207 collapsing. Distal end 207 consists of a plurality of lobes 268 (e.g., 268a-268c) connected by bridges 272 (e.g., 272a-272c) at about midpoints of lobes 268. This configuration creates additional holes 276 (e.g., 276a-276c) close to the end of a distal rim edge of tube 202. Holes 276 may be round, oval, or any other shape with a lengthwise diameter between about one-third of a diameter of inner lumen 208 to about two times the diameter of inner lumen 208. This configuration also results in a scalloped pattern into the distal rim edge. The depth of the indentations on the distal rim edge created by this scalloped pattern are preferably between about one-half of the diameter of inner lumen 208 to about equal to the diameter of inner lumen 208. The size of bridges 272 will be sufficient to prevent collapsing of lobes 268 due to forces encountered by distal end 207 during insertion into the pleural space. This configuration increases cross sectional area for suction at the tip of tube 202, which is where suction may be most effective for the removal of all pleural fluids. In addition, this configuration allows lobes 268 to bend slightly if presented with forces of a magnitude typically encountered during insertion, which may lead to less damage to the patient.

In a resting position, as shown in FIG. 6A, tube 202 may have a slight curve, and is flexible enough to be bent into an increased curve with a memory that would, absent tension bending tube 202 into an increased curve, tend toward assuming the original slight curve. The curvature of tube 202 may be increased to varying degrees, as shown for example in FIG. 6B. Preferably, tube 202 will have an initial point of curvature that is approximately at the point where an inserted tube exits the chest of a patient. (The location of this point may vary but may generally be between about 18 and 22 centimeters from distal end 207 when distal end 207 is in a preferred placement in the pleural space.) In order to avoid unnecessary curving of the portion of tube 202 that will usually remain outside the chest and to allow better control of positioning tube 202 in the pleural space, differential flexibility is included in tube 202. To this end, stiffness of tube 202 may be made greater in a proximal portion of tube 202 that will be outside the patient's chest when tube 202 is inserted to a desired position than a distal portion that will be all or mostly in the patient's chest, which will have greater flexibility compared with the proximal portion. This differential stiffness can be achieved by any suitable construction, including the inclusion of braiding material in the proximal portion of the wall of tube 202. Additional suitable processes for creating this differential flexibility include using a stiffer material for the proximal portion of tube 202 than the distal portion or creating a thicker wall for the proximal portion of tube 202 than the distal portion. A transition zone between stiffer and more flexible portions will form an approximate origin 284 of the arc.

Depth of insertion of tube 202 is indicated by circumferential stripes 288 (e.g., 288a-288c), which may also include measurement indicators (not shown). In addition or in the alternative, other ways of associating a particular stripe 288 with approximate depth, such as a correlation table, may be provided with chest tube assembly 200.

Lesser curvature channel 212 extends along lesser curvature 205. Pull line 216 is a flexible line, thread, string or wire, which can be polyethylene or other suitable material and is used to adjust the curve of tube 202. Pull line 216 is firmly attached at or near distal end 207 of tube 202 and runs through lesser curvature channel 212 until exiting approximately toward proximal end 206 of tube 202, preferably at or near handle 228. A suitable device, such as ring 236, for gripping or otherwise manipulating pull line 216 is preferably included at or near handle 228. Applying force on pull line 216 causes tube 202 to bend, increasing the curve continuously until a desired curve is attained. FIG. 6B shows chest tube assembly 200 in an increased curvature configuration. Lessening tension on pull line 216 allows the curve of tube 202 to decrease back toward the original slight curve. Pull line 216 and the flexibility of tube 202 thus allows the curvature of chest tube assembly 200 to be adjusted while distal end 207 is inserted in the pleural space.

Figure 8:
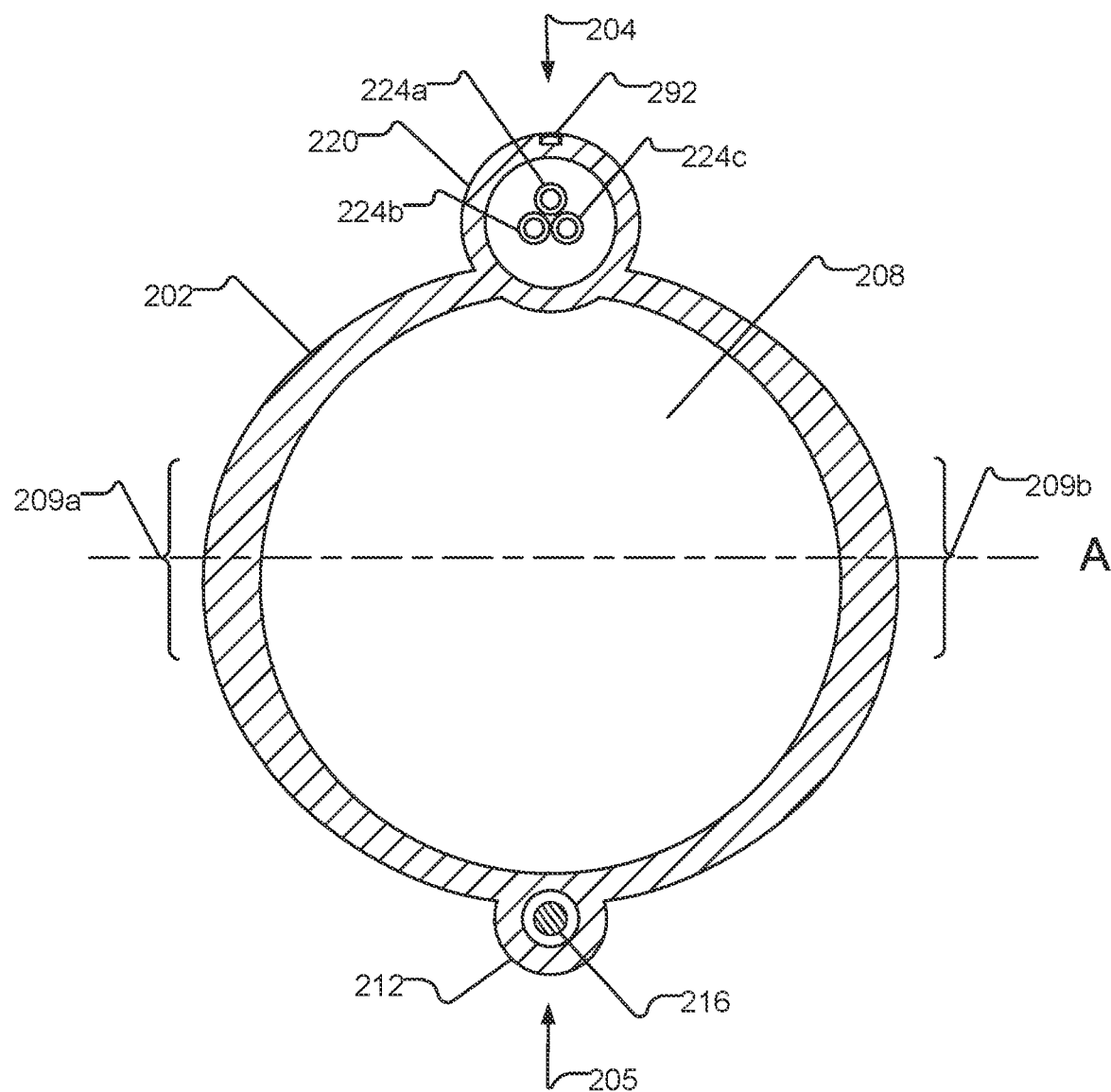
FIG. 8 is a cross-sectional view of the steerable chest tube of FIG. 6A

As seen in FIG. 8, tube 202 may have increased wall thickness at and around lateral portions 209 (e.g., 209a and 209b) that are about ninety degrees from greater curvature 204 and lesser curvature 205 along at least part of the length of tube 202 and preferably at least in the vicinity of the origin of the arc. In other words, tube 202 includes a sidewall with a ventral portion, a dorsal portion, a first lateral portion 209a and a second lateral portion 209b opposite first lateral portion 209a, and wherein for at least a portion of the sidewall of first lateral portion 209a and second lateral portion 209b are thicker than the ventral portion and the dorsal portion. First lateral portion 209a and second lateral portion 209b have similar thicknesses while the ventral portion and the lateral portion have similar, but smaller, thicknesses. This configuration will result in a favored bending axis (shown as line "A" in FIG. 8) so that tube 202 will reliably curve with lesser curvature 205 as the lesser curvature (and in a plane defined by the length of tube 202 in one dimension and a direction between greater curvature 204 and lesser curvature 205 in the other), thus providing for a more controllable and accurate placement of chest tube assembly 200.

In order to lock chest tube assembly 200 into a desired degree of curvature, any suitable mechanism can be used to hold pull line 216 in place. In one embodiment, shown in FIGS. 9A and 9B, a series of beads 240 (e.g., 240a-240h) are attached to pull line 216, with individual beads 240 about several millimeters apart, on a portion of pull line 216 that is external to lesser curvature channel 212. A groove with divots 296 (e.g., 296a-296e) is included on the lesser curvature side of handle 228. Beads 240 on pull line 216 can be selectively positioned into divots 296 in the groove such that series of beads 240 inserted into the groove will be firmly engaged and thus keep pull line 216 from sliding any further distally upon release of tension on pull line 216. (Beads 240 in divots 296 are prevented from moving distally be the distal walls of divots 296; these walls however include a gap sufficient to accommodate pull line 216, which is narrower than beads 240.) In this way, any curve of tube 202 created by placing tension on pull line 216 can be maintained without the need for a user to continuously apply tension. Because beads 240 are closely spaced along pull line 216, tube 202 can be locked in many different degrees of curvature. One example is shown in FIG. 9B. The resulting arc or curvature of tube 202 will be indicated by the distance pull line 216 has been retracted, which is discernable based on, for example, the most proximal bead 240 that is locked into groove 294. For example, retracting pull line 216 by a distance associated with one additional distal-most bead 240 being locked into groove 296 might indicate an added arc of 10 degrees on tube 202. Releasing all beads 240 from groove 296 will result in tube 202 approximately assuming the original slightly curved shape (shown in FIG. 6A). In addition, an optional mechanism may be included for preventing beads 240 from accidentally slipping out of the groove, so that if chest tube assembly is bumped or jostled after insertion and locking of curvature, pull line 216 will not move freely.

Cannulas 224 are included in greater curvature channel 220 and can be moved distally through greater curvature channel 220 a prescribed distance in order for the distal ends of cannulas 224 to extend out of greater curvature channel 220. In this way, cannulas 224 can be used to more efficiently deliver medications into the pleural space.

Figure 10A:
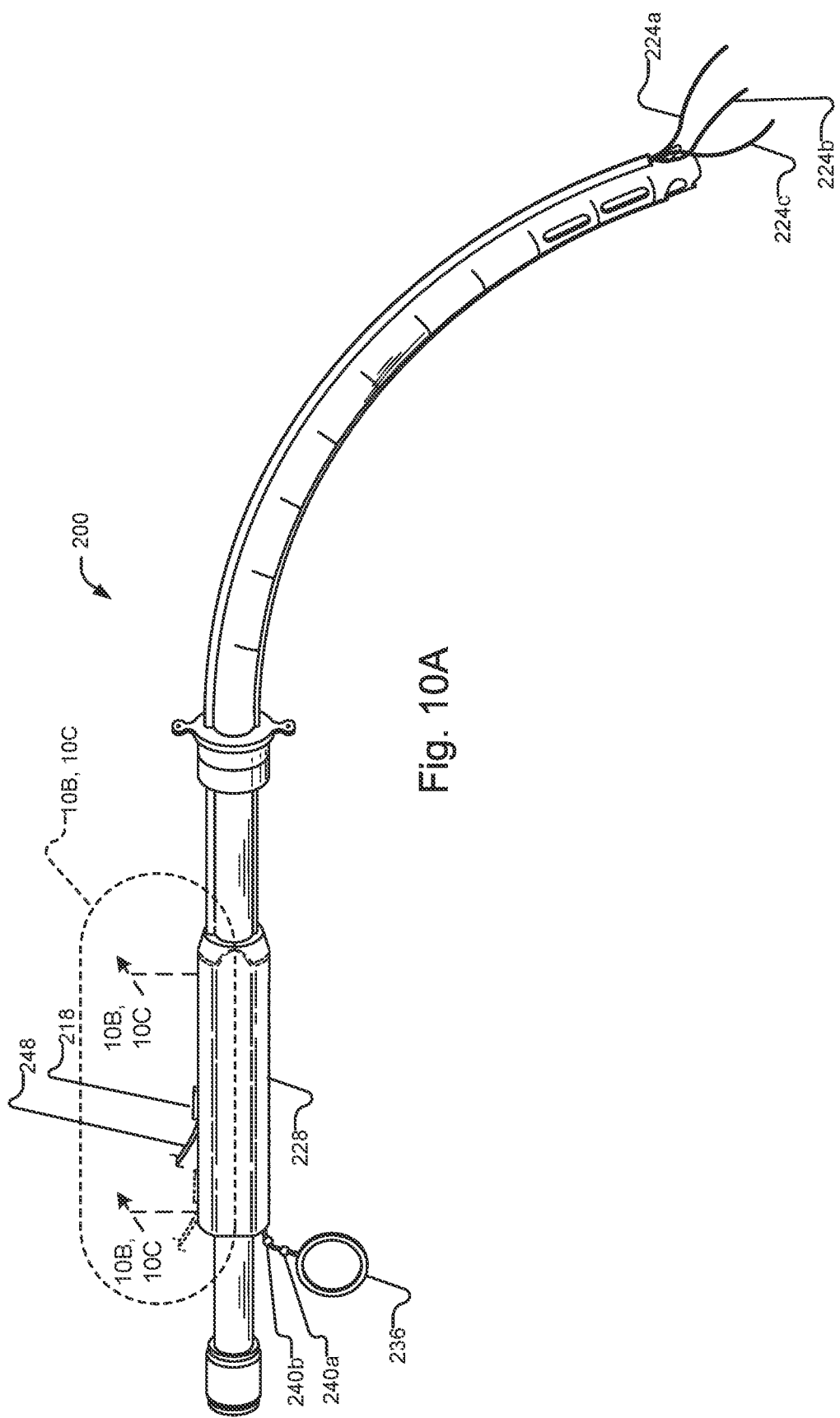
FIG. 10A shows a steerable chest tube with extended cannulas in accordance with an embodiment of the present invention.

Cannulas 224 may be braided together to form a braided bundle 248 of cannulas, which may be reinforced with a fine wire (not shown) to impart stiffness to facilitate the prescribed movement through greater curvature channel 220. A cannula extender assembly, shown in FIG. 10A-10D, includes a tab 218 or other suitable hand or finger activated mechanism on or near handle 228. Tab 218 is connected to a cylinder 242 with a lumen, and cannulas 224, or braided bundle 248 of cannulas, are attached to an inner surface of the lumen cylinder 242. A slot 246 is contained within handle 228 and is sized and configured to accommodate cylinder 242 within slot 246. Slot 246 at its distal end meets and is aligned with (or is contiguous with, or is part of) the lumen of greater curvature channel 220. A groove 250 is located above at least a portion of slot 246 and is designed and configured to allow tab 218 to be moved distally. Groove 250 has a length that is approximately the same as a distance that cannulas 224 are to be extended beyond distal end 207 into the pleural space, which preferably is about 3-5 centimeters. In a non-extended configuration, as shown in FIG. 10B, a proximal end of cylinder 242 is aligned with a proximal end of groove 250. When tab 218 is pushed distally through groove 250, as shown in FIG. 10D, cylinder 242 slides through slot 246 (and/or into the lumen of greater curvature channel 220), thereby causing cannulas 224 to extend beyond distal end 207.

A tight-fitting O-ring 254 surrounds cylinder 242 toward its distal end and forms a seal with slot 246 and/or the lumen of greater curvature channel 220, depending on the position of cylinder 242, to maintain sterility. O-ring 254 can be made of silicone or other appropriate materials.

A locking mechanism is preferably included for the cannula extender assembly to prevent the withdrawal of cannulas 224 that have been extended into the pleural space, which could violate sterility in greater curvature channel 220. Any suitable locking mechanism may be used. For example, the locking mechanism for the cannula extender assembly may include a semi-flexible flap 258 that extends at an angle proximally away and down from cylinder 242 (flap 258 is shown in detail in FIG. 10C). A bottom of slot 246 has a series of teeth 262 (e.g., 262a-262d) arranged to allow flap 258 to pass over when cylinder 242 is moved in a distal direction while preventing flap 258, and thus cylinder 242, from moving in a proximal direction. After chest tube assembly 200 has been removed from the patient, a tab or other device may be engaged to push flap 258 toward cylinder 242 and thereby allow cylinder 242 to slide in a proximal direction through slot 246. Preferably, to be engaged this mechanism would require a key or pin to be inserted into handle 228 in order to prevent accidental withdrawal of cylinder 242 while chest tube assembly 200 is inserted in a patient.

Distal end 207 of tube 202 may include an etched metal component (not shown) configured to scatter ultrasound waves, which facilitates localization of distal end 207 within the pleural space by the use of transcutaneous ultrasound, when available. Alternatively, distal end 207 may include a small embedded magnet (not shown) to allow detection by a portable magnetometer placed on the skin of the thorax of the patient. In addition, a longitudinal radiopaque marking line 292 (partially shown in FIG. 7) may extend along all of or a portion of the length of tube 202.

Figure 11:
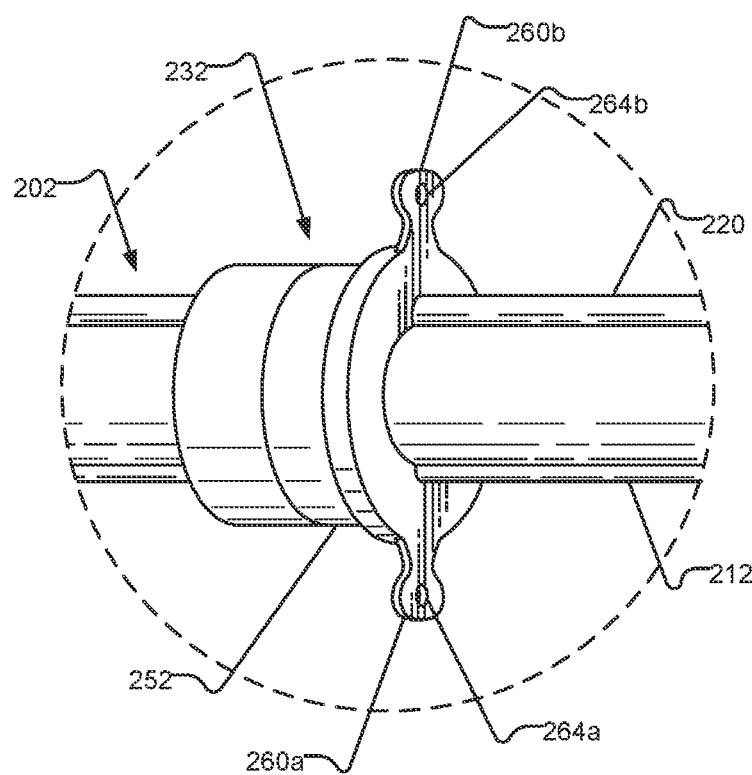
FIG. 11 is a detail view of a sewing collar of the steerable chest tube of FIG. 6A.

Turning to FIG. 11, a sewing collar 232 may be included on tube 202 that encircles a mid-portion of tube 202. Collar 232 is movable along tube 202 but can be secured anywhere along tube 202 by a suitable mechanism, preferably an adjustable friction or compression ring 252. Extending from collar 232 are flanges or wings 260 (e.g., 260a, 260b) with notches or holes 264 (e.g., 264a, 264b) to hold sutures to secure the placement of chest tube assembly 200 to the skin of the chest wall in order to hold chest tube assembly 200 in place once distal end 207 is in a desired location in the pleural space.

Figure 12A:
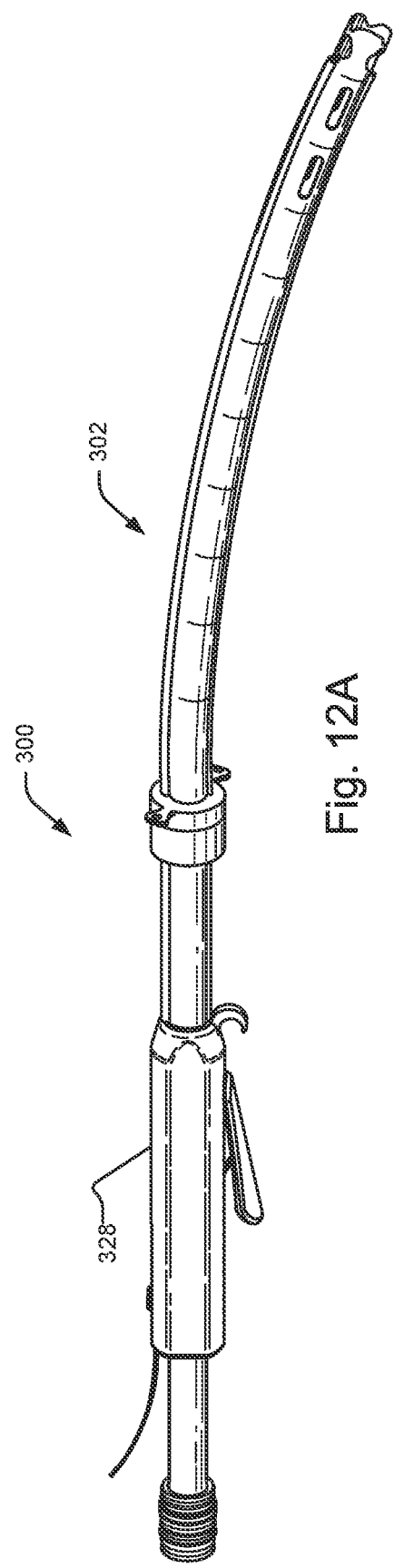

Another mechanism for applying tension to a pull wire of steerable chest tubes of the present invention and locking the pull wire in place is a linear ratchet assembly as shown in FIGS. 12A-12K. FIG. 12A shows a steerable chest tube assembly 300 with a handle 328 and a tube 302. FIGS. 12B-12D show the components of the linear ratchet assembly prior to the application of tension. A proximal end of a pull wire 316 is attached to a linear ratchet 309 that runs through a channel in handle 328. Linear ratchet 309 has a plurality of teeth 311 (e.g., 311a-311c) and a plurality of bias legs 313 (313a-313b) on an opposite side of linear ratchet 309 from teeth 311, wherein teeth 311 are designed to engage with a series of ramped teeth 321 (e.g., 321a) that are included within the channel of handle 318. A lever 315 is attached to an underside of handle 328 by hinge 317. One or more advancing rods 319 (e.g., 319a, 319b) are hingeably attached to a surface of lever 315 that generally faces linear ratchet 309. One end of advancing rods 319 will engage one of the plurality of bias legs 313 of linear ratchet 309 when lever 315 is depressed. Advancing rods 319 are attached to lever 315 such that advancing rods 319 can pivot proximally when lever 315 is depressed and will spring back to an initial orientation when lever 315 returns to an original position.

When lever 315 is depressed, as shown in FIGS. 12E-12G, advancing rods 319 engage one of the plurality of bias legs 313 and push linear ratchet 309 proximally, which causes pull wire 316 to be pulled in a proximal direction. As this happens, teeth 311 of linear ratchet 309 slide past ramped teeth 321 of handle 318 in a proximal direction while the orientation of teeth 311 and ramped teeth 321 prevents linear ratchet 309 from moving distally after lever 315 is no longer depressed (i.e., after advancing rods 319 is no longer applying force to bias legs 313). With the return of lever 315 to its original resting position, advancing rods 319 release bias leg 313 that had been pushed and engage the next more distal bias leg. Repeated depressions of lever 315 will thus advance pull wire 316 proximally, resulting in tension that will increase the arc on tube 302. The distance between bias legs 313 will determine how far pull wire 316 will be advanced with each depression of lever 315. For example, with appropriate spacing of bias legs 313, each depression of lever 315 will result in a 5 degree increase in the curve of tube 302. Therefore, the degree of curvature of tube 302 will be associated with the number of times lever 315 is depressed. As shown in FIG. 12H, after multiple depressions of lever 315, pull wire 316 has been maximally moved in the proximal direction.

The linear ratchet assembly tension mechanism further includes a release member 329 that includes a grip 327 to allow a user to engage release member 329, a series of teeth 331 that slidably engage an opposing second series of teeth 335 on handle 328, and a flat portion 333 opposite series of teeth 331 that engages teeth 311 of linear ratchet 309. When grip 327 is moved distally, teeth 331 slide along teeth 335 to force flat portion 333 downward. This downward motion causes flat portion 333 to engage linear ratchet 309, collapsing bias legs 313, which allows teeth 311 to disengage from ramped teeth 321 (as can be seen in FIGS. 12I and 12K), thereby allowing linear ratchet 309 to move freely. This allows pull wire 316 to move distally.

Another mechanism for applying tension to the pull wire of the steerable chest tube and holding the pull wire in position to secure a desired curvature of the tube is a tipping rings assembly. In the tipping rings assembly, the pull wire passes into a channel in the handle of the chest tube and through two tipping rings. Each tipping ring is attached to both sides of the channel, which allows the tipping rings to rotate freely. A lever is attached to the handle with a proximal hinge. An undersurface of the lever is in contact with the tipping rings and is shaped to move the tipping rings in opposite directions upon depression of the lever. The tipping rings return to initial positions when the lever is released. In operation, when the lever is in a resting position, the front tipping ring is perpendicular to the lever and does not engage the pull wire. The rear tipping ring is tilted, for example, at about a sixty-degree angle and has engaged and locked the pull wire in a fixed position when the lever is in a resting position. When the lever begins to be depressed, the front tipping ring begins to tilt and engages the pull wire while the rear tipping ring begins to assume a perpendicular orientation. With further depression of the lever, the front tipping ring rotates and pulls the pull wire proximally. With release of the lever, the rear tipping ring rotates and engages the pull wire, holding the pull wire in place while the front tipping ring once again assumes a perpendicular orientation, thereby disengaging the pull wire. Each depression of the lever will advance the pull wire a fixed distance. A small button, preferably on a side of the handle, will move both tipping rings to the perpendicular orientation and release the tension on the pull wire, allowing the tube move toward the initial curvature.

Other mechanisms for applying tension to the pull wire of the steerable chest tube and releasably locking the pull wire in position may be used including, for example, a retraction member assembly, in which a distal portion of the pull wire may be attached to a thicker retraction member with a length approximately equal to the total distance that the pull wire would be retracted to place the tube in its greatest curvature. The retraction member may be made of rubber or plastic or the like and includes a series of grips to enable manipulation of the retraction member by a user's hand. In a default closed setting, the retraction member is secured to the handle of the chest tube by a suitable mechanism, such as a clamp or other clutching mechanism, that would securely grasp a portion of the retraction member, such as the sides and a portion of the bottom, while another portion, such as another portion of the bottom, remains un-encompassed, so that the grips, for example, could be grasped by a user's hand (e.g., the grips may extend through the clamp downwardly from the handle). The clamp includes a release switch that would preferably be located such that a user could toggle the switch with the user's thumb while grasping the handle and maintaining the user's fingers in the grips between the default closed setting and an open setting. In the open setting, the retraction member would be able to move freely either proximally or distally within the clamping device while still being loosely supported within the clamp on the handle. Once the tube was in a desired degree of curvature, the switch actuated to put the clamp back into the closed setting, which would hold the reaction member in place in its new position. The retraction member could include markings, such as that would indicate distance the retraction member is retracted, degrees of tube curvature associated with the position of the retraction member, and/or representations of the tube showing the tube in the approximate curvature the tube will assume based on the current position of the retraction member. The particular marking that corresponds with the current position of the retraction member is indicated by an indicator on the handle, such as a line, that aligns with the particular marking, by being visible through a window on the handle, or by being the marking that is visible and the closest to the proximal end of the handle (i.e., if the proximal end of the retraction member exits on the handle or appears from beneath the handle as the retraction member is moved proximally.)

Another example of a mechanism for applying tension to the pull wire of the steerable chest tube and locking the pull wire in place is a spool assembly, in which a distal portion of the pull wire is attached to a spool and the spool is attached to or contained in the handle. When the spool is wound in a first direction, the pull wire will be retracted and the tube curvature will increase. Preferably, the spool may be wound by a user's thumb or finger while gripping the handle (so that only one hand is required to manipulate the pull wire). This is preferably accomplished indirectly via a toothed cylinder or gear that engages the spool and is easily manipulated by a thumb or finger of a user when the user is grasping the handle. In addition, the spool may include teeth that are engaged by a pawl so that in a default setting, the spool can only turn on the first direction. A switch or lever on the handle will allow a user to disengage the pawl, thereby allowing the spool to turn in both the first direction and a second direction. Thus, with the pawl disengaged, the pull line can move freely in both the proximal and the distal direction, and with the pawl engaged, the pull line can be locked in place to secure the tube in a desired curvature. An additional safety, such as a cover, for the switch may be included to prevent accidental disengagement of the pawl once the chest tube is secured in place (i.e., when the curvature of the tube no longer needs to be adjusted). Further, a display on the handle may be coordinated, via gears, for example, to indicate the status of the curve of the tube. For example, the number of turns of the spool in the first direction from the default position may be indicated, and/or any marking associated with the number of turns, such as length of pull line retracted, approximate degrees of curvature of the tube (in total or from the resting curve) based on the length of pull line retracted, or representations of the tube showing the tube in the approximate curvature the tube will assume based on the number of turns of the spool.

Figure 13A:
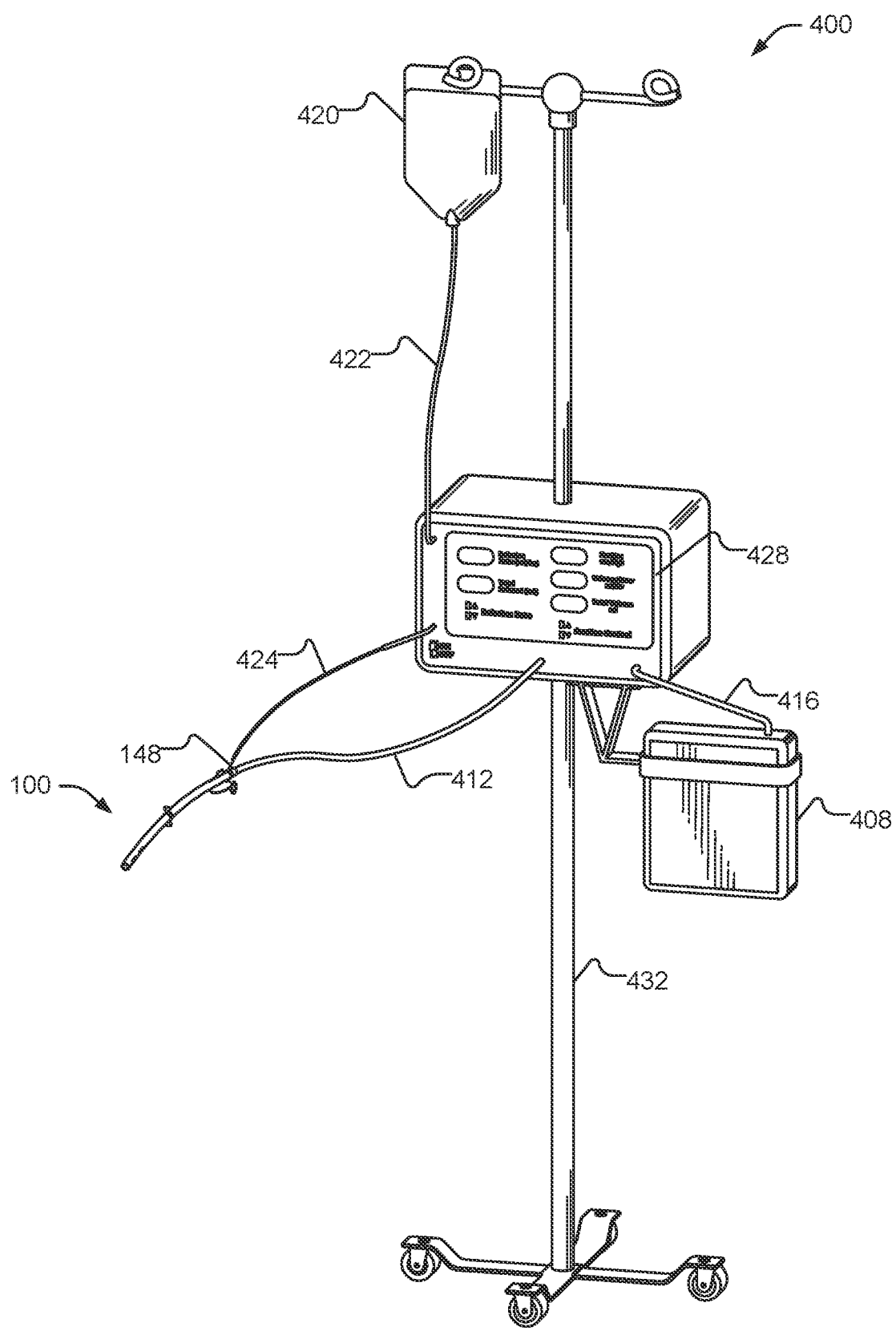
FIG. 13A is a perspective view of a suction/infusion device in accordance with the present invention.

A portable suction/irrigation device 400, shown in FIG. 13A, can be used to provide suction and irrigation for the chest tubes of the present invention. Suction device 400 includes a flowmeter to allow measurement of the fluid output of the chest tube, a reservoir 408 to receive and store fluid that has been drained through the main lumen of the chest tube, a connecting tube 412 to connect the chest tube to suction device 400, a reservoir line 416 to connect suction device 400 to reservoir 408, and any suitable pump, such as a piston driven or rotary suction source. An infusion pump is also included to irrigate fluid through the cannulas at an inputted flow rate. An infusion reservoir 420 holds infusion fluid that is connected to the infusion pump via infusion line in 422. From the infusion pump, infusion fluid is sent to the cannulas 124 by connecting line out 424.

Figure 13B:
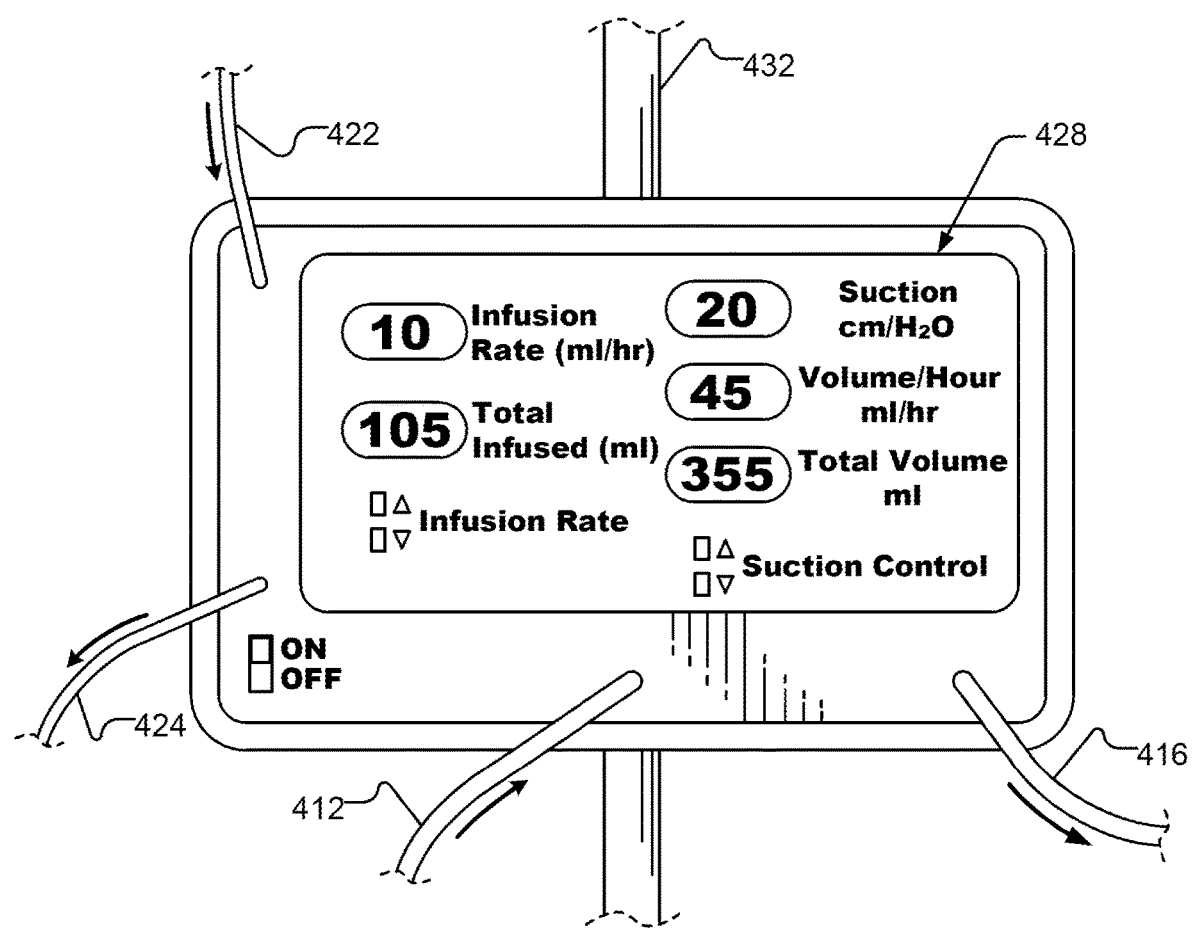
FIG. 13B is a detail view of an aspect of the suction/infusion device of FIG. 13A.

Suction device 400 may also include a battery for a back-up power supply as well as controls for adjusting infusion rate and amount of suction. In addition, a display screen, such as an LED screen 428, which is shown in greater detail in FIG. 13B, is included for displaying pertinent information such as reservoir levels, drainage rate, cumulative drained fluid volume, air leak rate, infusion rate, and cumulative infusion rate, as well as, optionally, touch screen controls. Suction device 400 may be secured near a patient on an IV pole 432 or similar, allowing suction device 400, along with an attached chest tube, to be transported with a patient as necessary.

In operation, with reference to chest tube assembly 100 for simplicity although it will be understood that the below discussion is applicable to any steerable chest tube of the present invention, a patient requiring hemothorax treatment is placed on his/her side. A small incision is made in the patient's chest and distal end 107 of tube 102 is inserted through the incision into the pleural space directed posteriorly with lesser curvature 105 facing down. Using a combination of insertion depth, differential curvature created via pull line 116, and rotation of chest tube assembly 100, distal end 107 can be placed in nearly any location in the pleural space, such as the lateral posterior diaphragmatic sulcus, which is the anticipated location of fluid accumulation when the patient is in the supine or semi-recumbent position. In non-emergent situations, an ultrasound or other detection probe might be placed on the chest wall during the chest tube insertion procedure. Embedded markers in the chest tube will enhance detection signals and allow the accurate positioning of distal end 107 of tube 102 in a desired position.

The controlled curve that can be generated by placing tension on pull line 116 ranges from an initial position, in which tube 102 will have a slight arc created at the time of production, e.g., preferably approximately 10-20°, to a maximal curvature of almost 180°. Once the desired curvature has been reached, the tension on pull line 116 can be locked by inserting pull line 116 into V-lock 144 at the appropriate bead 140 or be secured by any suitable locking mechanism, including the other tension and locking mechanisms described above for pull line 116.

Once distal end 107 has been placed in a desired location and the curve locked in place, adjustable collar 152 is moved along tube 102 to skin level, where collar 152 is secured in place on tube 102 by friction or compression ring 156 or another suitable device. With collar 152 secured in a desired location on tube 102, chest tube assembly 100 can be held in place with respect to the patient by suturing or stapling to the skin via holes 164 on flanges or wings 160.

When chest tube assembly 100 is secured in place, proximal end 106 of tube 102 is connected to suction device 400 and fluid can be drained into reservoir 408 and monitored by flowmeter. Valve mechanisms control the level of suction provided by the suction source. Reservoir 408 may be a disposable plastic reservoir and can be placed in line with chest tube assembly 100 and the suction source. In this way, reservoir 408 can be changed as required without the need to replace lines or flowmeters.

The degree of instability of the pressure associated with the suction source, which is indicative of line leakage, which is in turn directly correlated with air leak volume, can be displayed on LED screen 428.

In addition, optionally, pleural irrigation with anticoagulants or other medications can be established using chest tube assembly 100 and suction device 400. Push tab 118 can be actuated, such as by being moved in a distal direction, which will extend distal portions of cannulas 124 out of greater curvature channel 120 and beyond distal end 107 of tube 102 and into the pleural space a distance sufficient for infusing, which in a preferred embodiment may be approximately 3-5 cm. Preferably, a plurality of cannulas 124 will be braided together within greater curvature channel 120 to form a braided bundle of cannulas 148 and upon entering the pleural space, twisting braided bundle of cannulas 148 several times will separate and distribute cannulas 124 into the pleural space so that the delivery of anticoagulants, for example, will be more evenly dispersed. After advancement into the pleural space, cannulas 124 will be locked in place (as described above) to avoid withdrawal back up greater curvature channel 120 in order to prevent compromising the sterility of the system.

Infusion of anticoagulants, such as heparin or other medications, is controlled by a pump regulated micro-infusion device. Dilute anticoagulant (such as heparin) stored in infusion reservoir 420 can be infused by the infusion pump through cannulas 124 at a low rate into the pleural space. Infusion reservoir 420 is attached to infusion pump via infusion line in 422 and the irrigation fluids pumped via cassette or rotary tubing pumps. Infusion volume can be displayed on screen 428. Software included with screen 428 can continuously compare input infusion and output drainage volumes. If input infusion becomes greater than output drainage, suggesting possible plugging of the drainage tubing and accumulation of fluid in the chest, then the infusion pump will immediately shut-off and an alarm will sound.

In addition, control mechanisms will allow integrated control of the suction and infusion devices. As an example, this might allow sequential suction and medication infusion so as to allow time for the medication to dwell in the pleural space prior to aspiration through subsequent application of suction.

Suction device 400 can use power from electrical outlets but will have a back-up battery for short term required trips away from electrical outlets, such as for moving a patient from one area to another.

If repeated chest x-rays show an accumulation of fluid in the chest after two or three days, indicating inadequate drainage, then the anticoagulant solution can be changed to a thrombolytic infusion. Local anesthetics can also be infused through this same system to reduce pain induced by the presence of chest tube assembly 100.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A fluid removal system comprising:

a tube with a proximal end and a distal end, wherein the tube has a resting curve and is open on the proximal end and the distal end and includes a plurality of holes near the distal end;

a first channel along a greater curvature of the resting curve of the tube containing a plurality of cannulas with proximal ends and distal ends, wherein the distal ends of the plurality of cannulas can be extended beyond the first channel at the distal end of the tube;

a second channel along a lesser curvature of the resting curve of the tube containing a pull line with a distal end and a proximal end, wherein the distal end of the line is attached to the tube near the distal end of the tube and wherein a force applied to the pull line in a proximal direction causes the curve of the tube to reversibly increase; and a locking mechanism attached to the tube, the locking mechanism securing the pull line in place such that, when tension is placed on the pull line such that the curve of the tube is increased and the pull line is secured in the locking mechanism, the increased curve of the tube is maintained, wherein the locking mechanism includes a gripping device on the proximal end of the pull line, a plurality of evenly spaced beads attached to the pull line, and a V-lock attached to the tube, the V-lock designed and configured to prevent a selected one of the plurality of beads placed in the V-lock from moving distally when tension is on the pull line.

2. A fluid removal system comprising:

a tube with a proximal end and a distal end, wherein the tube has a resting curve and is open on the proximal end and the distal end and includes a plurality of holes near the distal end;

a first channel along a greater curvature of the resting curve of the tube containing a plurality of cannulas with proximal ends and distal ends, wherein the distal ends of the plurality of cannulas can be extended beyond the first channel at the distal end of the tube;

a second channel along a lesser curvature of the resting curve of the tube containing a pull line with a distal end and a proximal end, wherein the distal end of the line is attached to the tube near the distal end of the tube and wherein a force applied to the pull line in a proximal direction causes the curve of the tube to reversibly increase; and a locking mechanism attached to the tube, the locking mechanism securing the pull line in place such that, when tension is placed on the pull line such that the curve of the tube is increased and the pull line is secured in the locking mechanism, the increased curve of the tube is maintained, wherein the locking mechanism includes a handle on the tube, a gripping device attached to the proximal end of the pull line, a plurality of evenly spaced beads attached to the pull line, and a groove in the handle, wherein the groove includes a plurality of evenly spaced divots, each divot designed and configured to accept a one of the plurality of beads, wherein placement of at least a portion of the plurality of beads in a respective ones of the plurality of divots prevents the portion of the plurality of divots from moving distally when tension is on the pull line.

* * * * *